(12) United States Patent
Bajji et al.

(10) Patent No.: US 8,017,780 B1
(45) Date of Patent: Sep. 13, 2011

(54) THERAPEUTIC COMPOUNDS AND USES THEREOF

(75) Inventors: Ashok Bajji, Salt Lake City, UT (US); Se-Ho Kim, Salt Lake City, UT (US); Rajendra Tangallapally, Salt Lake City, UT (US)

(73) Assignee: Myrexis, Inc., Salt Lake City, UT (US)

( * ) Notice: Subject to any disclaimer, the term of this patent is extended or adjusted under 35 U.S.C. 154(b) by 0 days.

(21) Appl. No.: 12/577,042

(22) Filed: Oct. 9, 2009

Related U.S. Application Data

(60) Provisional application No. 61/104,170, filed on Oct. 9, 2008.

(51) Int. Cl.
*C07D 513/02* (2006.01)
*C07D 515/02* (2006.01)

(52) U.S. Cl. ...................................................... 546/118
(58) Field of Classification Search .................. 546/117, 546/118
See application file for complete search history.

(56) References Cited

U.S. PATENT DOCUMENTS

| 7,595,401 B2 | 9/2009 | Bajji et al. |
| 2010/0016586 A1 | 1/2010 | Bajji et al. |

FOREIGN PATENT DOCUMENTS

| WO | 2004005472 | * | 1/2004 |
| WO | 2007/134298 | | 11/2007 |
| WO | 2008/033747 A2 | | 3/2008 |
| WO | 2008/115262 A2 | | 9/2008 |
| WO | 2008/115719 A1 | | 9/2008 |
| WO | 2009/065035 | | 5/2009 |

\* cited by examiner

*Primary Examiner* — D M Seaman
*Assistant Examiner* — Niloofar Rahmani
(74) *Attorney, Agent, or Firm* — Kelly A. Echols; Herbert L. Ley, III; Myrexis IP Group

(57) ABSTRACT

The invention provides novel therapeutic compounds, pharmaceutical compositions comprising these compounds, and methods for using these compounds and compositions to treat diseases and disorders such as cancer.

20 Claims, No Drawings

THERAPEUTIC COMPOUNDS AND USES THEREOF

CROSS-REFERENCE TO RELATED APPLICATIONS

This application claims priority to U.S. Provisional Patent Application Ser. No. 61/104,170, filed Oct. 9, 2008, which is hereby incorporated by reference in its entirety.

FIELD OF THE INVENTION

The invention relates to novel therapeutic compounds that inhibit Heat Shock Protein 90 (Hsp90). The invention also relates to pharmaceutical compositions comprising these compounds, and methods of treating diseases and disorders, such as cancers, that respond favorably to the inhibition of Hsp90.

BACKGROUND OF THE INVENTION

Cancer is prevalent: Among United States citizens that live to be 70 years older and older, the probability of developing invasive cancer is 38% for females and 46% for males. According to the American Cancer Society, there will be about 1.4 million new cases of cancer in the United States alone in 2006. Although the five year survival rate for all cancers is now 65%, up from about 50% in the mid-nineteen seventies, cancer remains a leading killer today. Indeed, it is estimated that 565,000 people in the United States will die from cancer in 2006. (American Cancer Society, Surveillance Research, 2006). Although numerous treatments are available for various cancers, the fact remains that many cancers remain incurable, untreatable, and/or become resistant to standard therapeutic regimens. Thus, there is a clear need for new cancer treatments employing novel chemotherapeutic compounds.

Inhibitors of the molecular chaperone protein Hsp90 are being developed as one class of pharmacological weaponry in the anticancer chemotherapeutic arsenal. Consequently, there is a clear need for additional, novel, Hsp90 inhibitors for the treatment of diseases and disorders, such as cancer, that respond favorably to the inhibition of Hsp90.

BRIEF SUMMARY OF THE INVENTION

In one aspect, the present invention relates to compounds according to Formulae I and II:

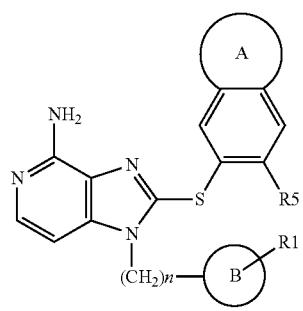

Formula I

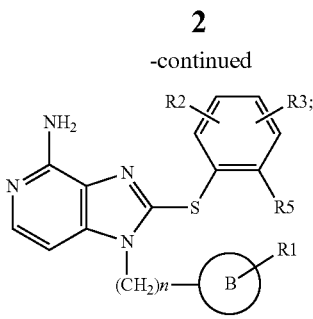

Formula II wherein, ring A is a saturated or partially saturated five to seven membered heterocyclic ring or a five to seven membered heteroaryl ring containing one or more hetero atoms independently selected from —O—, —N—, and —S—;

ring B is either a saturated or partially saturated five to seven membered heterocyclic ring or a five to seven membered heteroaryl ring containing one or more hetero atoms independently selected from —O—, —N—, and —S—, in any case ring B is attached to the remainder of the molecule via a ring carbon;

R1 is attached to a B-ring heteroatom and is selected from either —H, $C_{1-6}$ alkyl, branched $C_{1-6}$ alkyl, formyl, acetyl, carboxylates, or carboxamides, or when ring B contains a nitrogen, R1 can also be a natural or unnatural amino acid, D- and L-lactic acid, or hydroxy acetic acid, and, in such cases, the attachment of R1 to the B-ring is through a peptide bond formed between the carboxylic group of the substituent and a nitrogen in the B-ring;

R2 and R3 are independently selected from —H, halo, $C_{1-6}$ alkyl, $C_{1-6}$ alkoxy, acyl, sulfonyl, sulfamoyl, sulfonates, carboxylic acid (and esters thereof), carboxamides, and cycloalkyl;

n=0, 1, 2, 3, 4, or 5; and

R5 is selected from F, Cl, Br, I, $CF_3$, $NO_2$, CN, $CH_2NH_2$, $CH_2NHCH_3$, $CH_2NMe_2$, —$CO_2CH_3$, $CO_2C_2H_5$, —$NHCH_3$, and —$NMe_2$.

The compounds of the present invention include the compounds of the Formula I and Formula II as illustrated herein, as well as their geometric isomers, enantiomers, diastereomers, or racemates thereof. The compounds of the present invention also include pharmaceutically acceptable salts, prodrugs and solvates of all such compounds.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

1. Definitions

The term "bioisostere," as used herein, generally refers to compounds or moieties that have chemical and physical properties producing broadly similar biological properties. For example, —COOH bioisosteres include, but are not limited to, a carboxylic acid ester, amide, tetrazole, oxadiazole, isoxazole, hydroxythiadiazole, thiazolidinedione, oxazolidinedione, sulfonamide, sulfonylcarboxamide, phosphonic acid, phosphonamide, phosphinic acid, sulfonic acid, acyl sulfonamide, mercaptoazole, and cyanamide.

As used herein, the term "alkyl" as employed herein by itself or as part of another group refers to a saturated aliphatic hydrocarbon straight chain or branched chain group having, unless otherwise specified, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). An alkyl group may be in unsubstituted form or substituted form with one or more substituents (generally one to three substitutents except in the case of halogen substituents, e.g., perchloro). For example, a $C_{1-6}$ alkyl group ("lower alkyl") refers to a straight or branched aliphatic group containing 1 to 6 carbon atoms (e.g., methyl, ethyl, propyl, isopropyl, sec-butyl, tert-butyl, isobutyl, n-butyl, 3-pentyl, and hexyl), which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. An alkenyl group may be in unsubstituted form or substituted form with one or more substituents (generally one to three substitutents except in the case of halogen substituents, e.g., perchloro or perfluoroalkyls). For example, a $C_{1-6}$ alkenyl group refers to a straight or branched chain radical containing 1 to 6 carbon atoms and having at least one double bond between two of the carbon atoms in the chain (e.g., ethenyl, 1-propenyl, 2-propenyl, 2-methyl-1-propenyl, 1-butenyl and 2-butenyl, which may be optionally substituted).

The term "alkynyl" as used herein by itself or as part of another group means a straight or branched chain radical of 2-10 carbon atoms, unless the chain length is limited thereto, wherein there is at least one triple bond between two of the carbon atoms in the chain. An alkynyl group may be in unsubstituted form or substituted form with one or more substituents (generally one to three substitutents except in the case of halogen substituents, e.g., perchloro or perfluoroalkyls). For example, a $C_{1-6}$ alkynyl group refers to a straight or branched chain radical containing 1 to 6 carbon atoms and having at least one triple bond between two of the carbon atoms in the chain (e.g., ethynyl, 1-propynyl, 1-methyl-2-propynyl, 2-propynyl, 1-butynyl and 2-butynyl, which may be optionally substituted).

The term "carbocycle" as used herein by itself or as part of another group means cycloalkyl and non-aromatic partially saturated carbocyclic groups such as cycloalkenyl and cycloalkynyl. A carbocycle may be in unsubstituted form or substituted form with one or more substituents so long as the resulting compound is sufficiently stable and suitable for the treatment method of the present invention.

The term "cycloalkyl" as used herein by itself or as part of another group refers to a fully saturated 3- to 8-membered cyclic hydrocarbon ring (i.e., a cyclic form of an unsubstituted alkyl) alone ("monocyclic cycloalkyl") or fused to another cycloalkyl, cycloalkynyl, cycloalkenyl, heterocycle, aryl or heteroaryl ring (i.e., sharing an adjacent pair of carbon atoms with such other rings) ("polycyclic cycloalkyl"). Thus, a cycloalkyl may exist as a monocyclic ring, bicyclic ring, polycyclic or a spiral ring. When a cycloalkyl is recited as a substituent on a chemical entity, it is intended that the cycloalkyl moiety is attached to the entity through a carbon atom within the fully saturated cyclic hydrocarbon ring of the cycloalkyl. In contrast, a substituent on a cycloalkyl can be attached to any carbon atom of the cycloalkyl. A cycloalkyl may be in unsubstituted form or substituted form with one or more substituents so long as the resulting compound is sufficiently stable and suitable for the treatment method of the present invention. Examples of cycloalkyl groups include cyclopropyl, cyclobutyl, cyclopentyl, cyclohexyl and cycloheptyl.

The term "cycloalkenyl" as used herein by itself or as part of another group refers to a non-aromatic partially saturated 3- to 8-membered cyclic hydrocarbon ring (i.e., a cyclic form of an unsubstituted alkenyl) alone ("monocyclic cycloalkenyl") or fused to another cycloalkyl, cycloalkynyl, cycloalkenyl, heterocycle, aryl or heteroaryl ring (i.e., sharing an adjacent pair of carbon atoms with such other rings) ("polycyclic cycloalkenyl"). Thus, a cycloalkenyl may exist as a monocyclic ring, bicyclic ring, polycyclic or a spiral ring. When a cycloalkenyl is recited as a substituent on a chemical entity, it is intended that the cycloalkenyl moiety is attached to the entity through a carbon atom within the fully saturated cyclic hydrocarbon ring of the cycloalkenyl. In contrast, a substituent on a cycloalkenyl can be attached to any carbon atom of the cycloalkyl. A cycloalkenyl group may be unsubstituted or substituted with one or more substitutents. Examples of cycloalkenyl groups include cyclopentenyl, cycloheptenyl and cyclooctenyl.

The term "heterocycle" (or "heterocyclyl" or "heterocyclic") as used herein by itself or as part of another group means a saturated or partially saturated 3-7 membered non-aromatic cyclic ring formed with carbon atoms and from one to four heteroatoms independently selected from the group consisting of O, N, and S, wherein the nitrogen and sulfur heteroatoms can be optionally oxidized, and the nitrogen can be optionally quaternized ("monocyclic heterocycle"). The term "heterocycle" also encompasses a group having the non-aromatic heteroatom-containing cyclic ring above fused to another monocyclic cycloalkyl, cycloalkynyl, cycloalkenyl, heterocycle, aryl or heteroaryl ring (i.e., sharing an adjacent pair of carbon atoms with such other rings) ("polycyclic heterocycle"). Thus, a heterocycle may exist as a monocyclic ring, bicyclic ring, polycyclic or a spiral ring. When a heterocycle is recited as a substituent on a chemical entity, it is intended that the heterocycle moiety is attached to the entity through an atom within the saturated or partially saturated ring of the heterocycle. In contrast, a substituent on a heterocycle can be attached to any suitable atom of the heterocycle. In a "saturated heterocycle" the non-aromatic heteroatom-containing cyclic ring described above is fully saturated, whereas a "partially saturated heterocycle" contains one or more double or triple bonds within the non-aromatic heteroatom-containing cyclic ring regardless of the other ring it is fused to. A heterocycle may be in unsubstituted form or substituted form with one or more substituents so long as the resulting compound is sufficiently stable and suitable for the treatment method of the present invention.

Some examples of saturated or partially saturated heterocyclic groups include furanyl, tetrahydrofuranyl, thiophenyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

As used herein, "aryl" by itself or as part of another group means an all-carbon aromatic ring with up to 7 carbon atoms in the ring ("monocyclic aryl"). In addition to monocyclic aromatic rings, the term "aryl" also encompasses a group having the all-carbon aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic aryl"). When an aryl is recited as a substituent on a chemical entity, it is intended that the aryl moiety is attached to the entity through an atom within the all-carbon aromatic ring of the aryl. In contrast, a substituent on an aryl can be attached to any suitable atom of the aryl. Examples, without limitation, of aryl groups are phenyl, naphthalenyl and anthracenyl. An aryl may be in unsubstituted form or substituted form with one or more substituents so long as the resulting compound is sufficiently stable and suitable for the treatment method of the present invention.

The term "heteroaryl" as employed herein refers to a stable aromatic ring having up to 7 atoms with 1, 2, 3 or 4 heteroatoms which are oxygen, nitrogen or sulfur or a combination thereof ("monocyclic heteroaryl"). In addition to monocyclic hetero aromatic rings, the term "heteroaryl" also encompasses a group having the monocyclic hetero aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic heteroaryl"). When a heteroaryl is recited as a substituent on a chemical entity, it is intended that the heteroaryl moiety is attached to the entity through an atom within the hetero aromatic ring of the heteroaryl. In contrast, a substituent on a heteroaryl can be attached to any suitable atom of the heteroaryl. A heteroaryl may be in unsubstituted form or substituted form with one or more substituents so long as the resulting compound is sufficiently stable and suitable for the treatment method of the present invention.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-c]pyrimidin-4-one, pyrazolo[1,5-c]pyrimidinyl, including without limitation pyrazolo[1,5-c]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

As used herein, the term "halo" refers to chloro, fluoro, bromo, and iodo.

As used herein, the term "hydro" refers to a hydrogen atom (—H group).

As used herein, the term "hydroxyl" refers to an —OH group.

As used herein, unless otherwise specified, the term "alkoxy" refers to a —O—$C_{1-12}$ alkyl.

As used herein, the term "cycloalkyloxy" refers to an —O-cycloalkyl group.

As used herein, the term "aryloxy" refers to an —O-aryl group.

As used herein, the term "heteroaryloxy" refers to both an —O-heteroaryl group.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy. An acyloxy group may be unsubstituted or substituted form with one or more substituents so long as the resulting compound is sufficiently stable and suitable for the treatment method of the present invention.

As used herein, the term "mercapto" group refers to an —SH group.

As used herein, the term "alkylthio" group refers to an —S-alkyl group.

As used herein, the term "arylthio" group refers to both an —S-aryl group.

The term "arylalkyl" is used herein to mean an above-defined alkyl group substituted by an aryl group defined above. Examples of arylalkyl groups include benzyl, phenethyl and naphthylmethyl, etc. An arylalkyl group may be unsubstituted or substituted with one or more substituents so long as the resulting compound is sufficiently stable and suitable for the treatment method of the present invention.

The term "heteroarylalkyl" is used herein to mean an alkyl group defined above substituted by any heteroaryl groups. A heteroarylalkyl may be unsubstituted or substituted with one or more substituents so long as the resulting compound is sufficiently stable and suitable for the treatment method of the present invention.

The term "arylalkenyl" is used herein to mean an alkenyl group defined above substituted by any aryl groups defined above.

The term "heteroarylalkenyl" is used herein to mean any of the above-defined alkenyl groups substituted by any of the above-defined heteroaryl groups.

The term "arylalkynyl" is used herein to mean any of the above-defined alkynyl groups substituted by any of the above-defined aryl groups.

The term "heteroarylalkynyl" is used herein to mean any of the above-defined alkynyl groups substituted by any of the above-defined heteroaryl groups.

The term "aryloxy" is used herein to mean aryl-O— wherein aryl is as defined above. Useful aryloxy groups include phenoxy and 4-methylphenoxy.

The term "heteroaryloxy" is used herein to mean heteroaryl-O— wherein heteroaryl is as defined above.

The term "arylalkoxy" is used herein to mean an alkoxy group substituted by an aryl group as defined above. Useful arylalkoxy groups include benzyloxy and phenethyloxy.

"Heteroarylalkoxy" is used herein to mean any of the above-defined alkoxy groups substituted by any of the above-defined heteroaryl groups.

"Haloalkyl" means an alkyl group substituted by one or more (1, 2, 3, 4, 5 or 6) fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen which is in turn attached to the main structure, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refer to a cycloalkyl group in which one of the carbon atoms which form the ring has a "=O" bonded to it; i.e. one of the ring carbon atoms is a —C(=O)-group.

As used herein, the term "thiocarbonyl" group refers to a —C(=S)R" group, with R" as defined herein.

As used herein, the term "O-carboxy" group refers to a R"C(=O)O-group, with R" as defined herein.

As used herein, the term "C-carboxy" group refers to a —C(=O)OR" groups with R" as defined herein.

As used herein, the term "ester" is a C-carboxy group, as defined herein, wherein R" defined above except that it is not hydro (e.g., methyl, ethyl, lower alkyl).

As used herein, the term "C-carboxy salt" refers to a —C(=O)O⁻M⁺ group wherein M⁺ is selected from the group consisting of lithium, sodium, magnesium, calcium, potassium, barium, iron, zinc and quaternary ammonium.

As used herein, the term "acetyl" group refers to a —C(=O)CH$_3$ group.

As used herein, the term "carboxyalkyl" refers to —(CH$_2$)$_r$C(=O)OR" wherein r is 1-6 and R" is as defined above.

As used herein, the term "carboxyalkyl salt" refers to a —(CH$_2$)$_n$C(=O)O⁻M⁺ wherein M⁺ is selected from the group consisting of lithium, sodium, potassium, calcium, magnesium, barium, iron, zinc and quaternary ammonium.

As used herein, the term "carboxylic acid" refers to a C-carboxy group in which R" is hydro.

As used herein, the term "trihalomethanesulfonyl" refers to a X$_3$CS(=O)$_2$-group with X is a halo as defined above.

As used herein, the term "cyano" refers to a —C≡N group.

As used herein, the term "cyanato" refers to a —CNO group.

As used herein, the term "isocyanato" refers to a —NCO group.

As used herein, the term "thiocyanato" refers to a —CNS group.

As used herein, the term "isothiocyanato" refers to a —NCS group.

As used herein, the term "sulfinyl" refers to a —S(=O)R" group, with R" as defined herein.

As used herein, the term "sulfonyl" refers to a —S(=O)$_2$R" group, with R" as defined herein.

As used herein, the term "sulfonamide" refers to a —S(=O)$_2$N(R$^{17}$)(R$^{18}$), with R$^{17}$ and R$^{18}$ as defined herein.

As used herein, the term "trihalomethanesulfonamido" refers to a X$_3$CS(=O)$_2$NR$^{17}$-group with X is halo as defined above and R$^{17}$ as defined herein.

As used herein, the term "O-carbamyl" refers to a —OC(=O)N(R$^{17}$)(R$^{18}$) group with R$^{17}$ and R$^{18}$ as defined herein.

As used herein, the term "N-carbamyl" refers to a R$^{18}$OC(=O)NR$^{17}$— group, with R$^7$ and R$^{18}$ as defined herein.

As used herein, the term "O-thiocarbamyl" refers to a —OC(=S)N(R$^{17}$)(R$^{18}$) group with R$^{17}$ and R$^{18}$ as defined herein.

As used herein, the term "N-thiocarbamyl" refers to a R$^{17}$OC(=S)NR$^{18}$— group, with R$^{17}$ and R$^{18}$ as defined herein.

As used herein, the term "amino" refers to an —N(R$^{17}$)(R$^{18}$) group, with R$^{17}$ and R$^{18}$ as defined herein.

As used herein, the term "aminoalkyl" refers to a moiety wherein an amino group as defined herein attached through the nitrogen atom to an alkyl group as defined above.

As used herein, the term "C-amido" refers to a —C(=O)N(R$^{17}$)(R$^{18}$) group with R$^{17}$ and R$^{18}$ as defined herein. An "N-amido" refers to a R$^{17}$C(=O)NR$^{18}$— group with R$^{17}$ and R$^{18}$ as defined herein.

As used herein, the term "C-amidoalkyl" refers to a —C$_{1-6}$ alkyl-CO$_2$N(R$^{17}$)(R$^{18}$) group with R$^{17}$ and R$^{18}$ as defined herein.

As used herein, the term "nitro" refers to a —NO$_2$ group.

As used herein, the term "quaternary ammonium" refers to a —⁺N(R$^{17}$)(R$^{18}$)(R$^{19}$) group wherein R$^{17}$, R$^{18}$, and R$^{19}$ are as defined herein.

R$^{17}$, R$^{18}$, and R$^{19}$ are independently selected from the group consisting of hydro and unsubstituted lower alkyl.

As used herein, the term "methylenedioxy" refers to a —OCH$_2$O— group wherein the oxygen atoms are bonded to adjacent ring carbon atoms.

As used herein, the term "ethylenedioxy" refers to a —OCH$_2$CH$_2$O— group wherein the oxygen atoms are bonded to adjacent ring carbon atoms.

2. Therapeutic Compounds

In general, the present invention comprises a compound according to Formulae I or II:

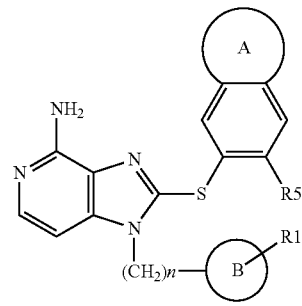

Formula I

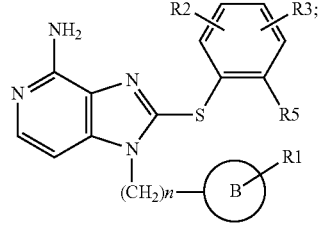

Formula II wherein, ring A is a saturated or partially saturated five to seven membered heterocyclic ring, or a five to seven membered heteroaryl ring, containing one or more hetero atoms independently selected from —O—, —N—, and —S—;

ring B is either a saturated or partially saturated five to seven membered heterocyclic ring, or a five to seven membered heteroaryl ring, containing one or more hetero atoms independently selected from —O—, —N—, and —S—, wherein ring B is attached to the remainder of the molecule via a ring carbon;

R1 is attached to a B-ring heteroatom and is selected from H, C$_{1-6}$ alkyl, branched C$_{1-6}$ alkyl, formyl, acetyl, carboxylate, carboxamide, a natural or unnatural amino acid, D- or L-lactic acid, or hydroxy acetic acid;

R2 and R3 are independently selected from —H, halo, C$_{1-6}$ alkyl, C$_{1-6}$ alkoxy, acyl, sulfonyl, sulfamoyl, sulfonates, carboxylic acid (and esters thereof), carboxamides, and cycloalkyl;

n=0, 1, 2, 3, 4, or 5; and

R5 is selected from F, Cl, Br, I, CF$_3$, NO$_2$, CN, CH$_2$NH$_2$, CH$_2$NHCH$_3$, CH$_2$NMe$_2$, —CO$_2$CH$_3$, CO$_2$C$_2$H$_5$, —NHCH$_3$, and —NMe$_2$.

In some embodiments of the invention, a compound is provided having a structure according to Formula I wherein n, rings A and B, and substituents R1 and R5, are as defined above.

In some embodiments of the invention, a compound is provided having a structure according to Formula II wherein n, ring B, and substituents R1, R2, R3 and R5, are as defined above.

In some embodiments of the invention n is 2. In other embodiments, n is 3.

In some embodiments of the invention, n is 1, 2, or 3 and R5 is selected from F, Cl, Br, I, $CF_3$, $NO_2$, —NMe, and CN.

In some embodiments of the invention the A ring is a fused, 5 or 6 membered ring containing one or two oxygens. In particular subembodiments of these embodiments the resulting fused bicyclic ring system attached to the remainder of the molecule via the linking —S— group is either benzo[1,3]dioxole, 2,3-dihydro-benzo[1,4]dioxine, 2,3-dihydro-benzofuran, or benzofuran.

In some embodiments of the invention, the B ring is an optionally substituted piperidine ring, attached to the core of the molecule via either the 2, 3, or 4 position, but not the 1 position.

In other embodiments of the invention, the B ring is an optionally substituted pyrrolidine ring, attached to the core of the molecule via either the 2 or 3 position, but not the 1 position.

In still other embodiments of the invention, the B ring is an optionally substituted homopiperidine ring, attached to the core of the molecule via either the 2, 3, 4, or 5 position, but not the 1 position.

In still other embodiments of the invention, the B ring is an optionally substituted thiophene ring, attached to the core of the molecule via either the 2 or 3 position, but not the 1 position.

In still other embodiments of the invention, ring B is a piperidine, pyrrolidine, homopiperidine, or thiophene ring.

In some embodiments of the invention, R1 is attached to a B-ring heteroatom and is selected from either —H, $C_{1-6}$ alkyl, branched $C_{1-6}$ alkyl, formyl, acetyl, carboxylates, or carboxamides, or when ring B contains a nitrogen, R1 is optionally a natural or unnatural amino acid, D- or L-lactic acid, or hydroxy acetic acid, wherein, the attachment of R1 to the B-ring is through a peptide bond formed between the carboxylic group of R1 and the nitrogen in the B-ring;

In specific embodiments of the invention, R1 is:

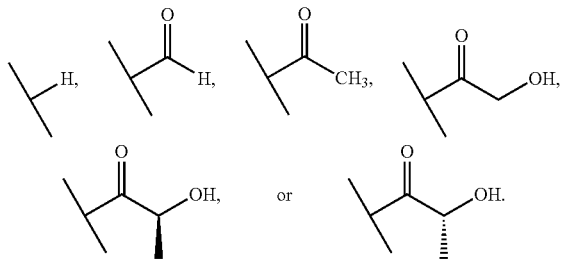

In one aspect of the present invention, the compounds of Formula I are more specifically compounds according to Formula III:

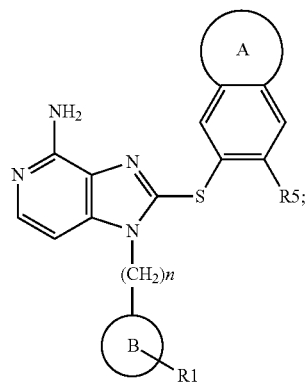

Formula III wherein, n=1, 2, or 3;
wherein, ring A is a saturated or partially saturated five to seven membered heterocyclic ring or a five to seven membered heteroaryl ring containing one or more hetero atoms independently selected from —O—, —N—, and —S—;
ring B is either a saturated or partially saturated five to seven membered heterocyclic ring or a five to seven membered heteroaryl ring containing one or more hetero atoms independently selected from —O—, —N—, and —S—, in any case ring B is attached to the remainder of the molecule via a ring carbon;
R1 is selected from either H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid; and
R5 is selected from F, Cl, Br, I, $CF_3$, $NO_2$, —$NMe_2$, and CN.

In certain embodiments of this aspect, the present invention comprises compounds of Formula III in which ring B is a piperidine, pyrrolidine, homopiperidine, or thiophene ring.

In certain embodiments of this aspect, the present invention comprises compounds of Formula III in which ring B is selected from an optionally substituted (1) pyrrolidine ring attached to the compound core via the 2 or 3 position; (2) a piperidine ring attached to the compound core via the 2, 3 or 4 position; or (3) a homopiperidine attached to the compound core via the 2, 3, 4 or 5 position. In all of these embodiments the B ring is never attached to the remainder of the compound via the 1 position (i.e., via the ring nitrogen).

In certain embodiments of this aspect, the present invention comprises compounds of Formula III in which ring A is selected from a fused 5 or 6 membered heterocycle containing one or two —O— groups.

In certain embodiments of this aspect, the present invention comprises compounds of Formula III, wherein n is 1, 2, or 3 and R5 is selected from F, Cl, Br, I, $CF_3$, $NO_2$, —$NMe_2$, and CN.

In certain embodiments of this aspect, the present invention comprises compounds of Formula III in which R1 is attached to a B-ring heteroatom and is selected from —H, $C_{1-6}$ alkyl, branched $C_{1-6}$ alkyl, formyl, acetyl, carboxylates, and carboxamides, or when ring B contains a nitrogen, R1 optionally is a natural or unnatural amino acid, D- or L-lactic acid, or hydroxy acetic acid, wherein the attachment of R1 to the B-ring is through a peptide bond formed between the carboxylic group of R1 and the nitrogen in the B-ring;

In certain embodiments of this aspect, the present invention comprises compounds of Formula III in which R5 is selected from —$NMe_2$, F, Cl, Br, and I.

In a subaspect of the invention, the compounds according to Formula III are more particularly compounds according to Formula IV:

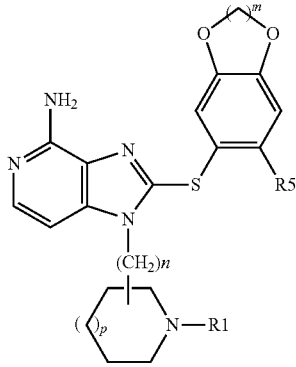

Formula IV wherein, n=1, 2, or 3;
m=1 or 2;
p=0, 1, or 2; and
R1 and R5 are as defined for Formula III, above.

In some embodiments of this subaspect of the invention n is 2. In other embodiments n is 3.

In some embodiments of this subaspect of the invention, R5 is —NMe$_2$, F, Cl, Br, or I.

In some embodiments of this subaspect of the invention, the R1 substituent is:

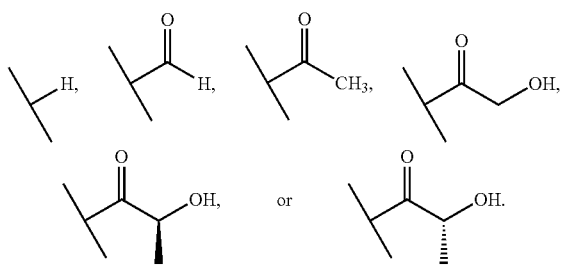

In another aspect of the present invention, the compounds of Formula II are more specifically compounds according to Formula V:

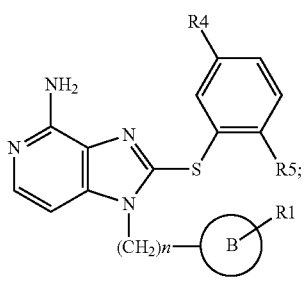

Formula V wherein, n=1, 2, or 3;
ring B is either a saturated or partially saturated five to seven membered heterocyclic ring or a five to seven membered heteroaryl ring containing one or more hetero atoms independently selected from —O—, —N—, and —S—, in any case ring B is attached to the remainder of the molecule via a ring carbon;

R1 is selected from H, C$_{1-6}$ alkyl, branched C$_{1-6}$ alkyl, formyl, acetyl, carboxylate, carboxamide, a natural or unnatural amino acid, D- or L-lactic acid, and hydroxy acetic acid;

R4 is selected from —H, halo, C$_{1-6}$ alkyl, C$_{1-6}$ alkoxy, acyl, sulfonyl, sulfamoyl, sulfonate, carboxylic acid, ester, carboxamide, and cycloalkyl; and R5 is selected from F, Cl, Br, I, CF$_3$, NO$_2$, —NMe$_2$, and CN.

In certain embodiments of this aspect, the present invention comprises compounds of Formula V in which ring B is selected from an optionally substituted (1) pyrrolidine ring attached to the compound core via the 2 or 3 position; (2) a piperidine ring attached to the compound core via the 2, 3 or 4 position; or (3) a homopiperidine attached to the compound core via the 2, 3, 4 or 5 position. In all of these embodiments the B ring is never attached to the remainder of the compound via the 1 position (i.e., via the ring nitrogen).

In certain embodiments of this aspect, the present invention comprises compounds of Formula V in which R5 is selected from —NMe$_2$, F, Cl, Br, or I.

In certain embodiments of this aspect, the present invention comprises compounds of Formula V in which R4 is selected from C$_{1-6}$ alkoxy, acyl, sulfonyl, sulfamoyl, sulfonate, carboxylic acid, ester, carboxamide, or cycloalkyl.

In specific embodiments of this aspect, the present invention comprises compounds of Formula V in which R4 is C$_{1-6}$ alkoxy.

In specific embodiments of this aspect, the present invention comprises compounds of Formula V in which R4 is methoxy.

In specific embodiments of this aspect, when Ring B is a nitrogen heterocycle and R1 is selected from natural and unnatural amino acids, D and L-lactic acid, and hydroxy acetic acid, then a peptide bond is formed through the carboxylic group of R1 and the ring B nitrogen;

In some embodiments of the invention, the B ring is an optionally substituted piperidine ring, attached to the core of the molecule via either the 2, 3, or 4 position, but not the 1 position.

In other embodiments of the invention, the B ring is an optionally substituted pyrrolidine ring, attached to the core of the molecule via either the 2 or 3 position, but not the 1 position.

In still other embodiments of the invention, the B ring is an optionally substituted homopiperidine ring, attached to the core of the molecule via either the 2, 3, 4, or 5 position, but not the 1 position.

In still other embodiments of the invention, the B ring is an optionally substituted thiophene ring, attached to the core of the molecule via either the 2 or 3 position, but not the 1 position.

In specific embodiments of the invention, R1 is:

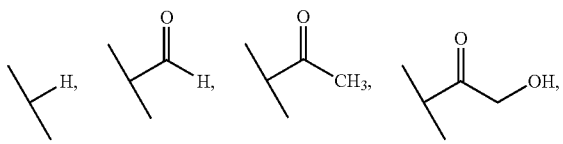

-continued

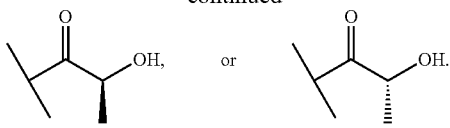

In a subaspect of the invention, the compounds according to Formula V are more particularly compounds according to Formula VI:

Formula VI

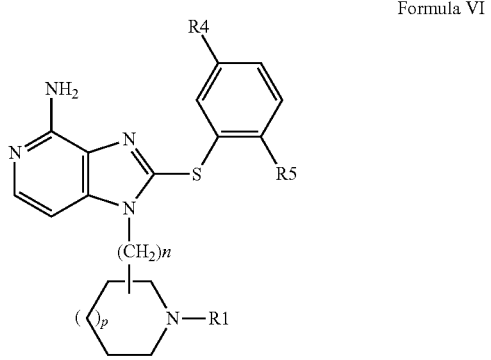

wherein, n=1, 2, or 3;
p=0, 1, or 2;
R1 and R5 are as defined for Formula V, above; and
R4 is selected from —H, halo, $C_{1-6}$ alkyl, $C_{1-6}$ alkoxy, acyl, sulfonyl, sulfamoyl, sulfonate, carboxylic acid, ester, carboxamide, and cycloalkyl.

In some embodiments of this subaspect of the invention n is 2. In other embodiments n is 3.

In some embodiments of this subaspect of the invention, R5 is —NMe$_2$, F, Cl, Br, or I.

In some embodiments of this subaspect of the invention, the R1 substituent is:

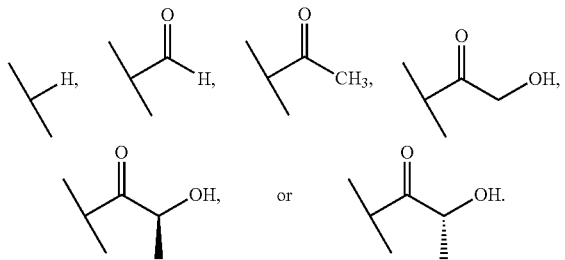

In some embodiments of this subaspect of the invention R4 is $C_{1-6}$ alkoxy.

In specific embodiments of this subaspect of the invention R4 is methoxy.

The compounds of the present invention include the compounds of the Formulae I through VI as illustrated herein, as well as their geometric isomers, enantiomers, diastereomers, or racemates thereof. The compounds of the present invention also include pharmaceutically acceptable salts, prodrugs and solvates of all such compounds.

In preferred embodiments, compounds of Formulae I through VI, having an IC$_{50}$ of less than 2,500 nM, 500 nM, 300 nM, 200 nM, preferably less than 100 nM, and most preferably less than 50 nM, as determined by the Hsp90 binding assay, which is described in the "Biological and Pharmacological Assays and Examples" section below, are used as the therapeutic compounds of the invention.

As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human a pharmaceutical composition comprising an effective amount of a compound according to the present invention.

A pharmaceutically acceptable salt of the compound of the present invention is exemplified by a salt with an inorganic acid and/or a salt with an organic acid that are known in the art. In addition, pharmaceutically acceptable salts include acid salts of inorganic bases, such as salts containing alkaline cations, alkaline earth cations, as well as acid salts of organic bases. Their hydrates, solvates, and the like are also encompassed in the compound of the present invention. In addition, N-oxide compounds are also encompassed in the compound of the present invention.

Additionally, as implied above, the compounds of the present invention can contain asymmetric carbon atoms and can therefore exist in racemic and optically active forms. Thus, optical isomers or enantiomers, racemates, and diastereomers of the depicted compounds are also encompassed. The methods of present invention include the use of all such isomers and mixtures thereof. The present invention encompasses any isolated racemic or optically active form of compounds described above, or any mixture thereof, which possesses therapeutic activity, particularly anti-cancer activity.

In preferred embodiments, compounds of Formulae I through VI are provided having an IC$_{50}$ of less than 2,500 nM, 500 nM, 300 nM, 200 nM, preferably less than 100 nM, and most preferably less than 50 nM, as determined in the Hsp90 binding assay described in the "Biological and Pharmacological Assays and Examples" section below.

Unless specifically stated otherwise or indicated by a bond symbol (dash or double dash), the connecting point to a recited group will be on the right-most stated group. Thus, for example, a hydroxyalkyl group is connected to the main structure through the alkyl and the hydroxyl is a substituent on the alkyl.

In the compounds of the invention, reference to any bound hydrogen atom can also encompass a deuterium atom bound at the same position. Substitution of hydrogen atoms with deuterium atoms is conventional in the art. See, e.g., U.S. Pat. Nos. 5,149,820 & 7,317,039, which are incorporated by reference herein in their entirety. Such deuteration sometimes results in a compound that is functionally indistinct from its hydrogenated counterpart, but occasionally results in a compound having beneficial changes in the properties relative to the non-deuterated form. For example, in certain instances, replacement of specific bound hydrogen atoms with deuterium atoms dramatically slows the catabolism of the deuterated compound, relative to the non-deuterated compound, such that the deuterated compound exhibits a significantly longer half-life in the bodies of individuals administered such compounds. This is particularly so when the catabolism of the hydrogenated compound is mediated by cytochrome P450 systems. See Kushner et al., *Can. J. Physiol. Pharmacol.* (1999) 77:79-88, which is incorporated by reference herein in its entirety.

3. Pharmaceutical Compositions

In another aspect, the present invention further provides a medicament or a pharmaceutical composition having a therapeutically or prophylactically effective amount of a therapeutic compound according to the present invention.

Typically, therapeutic compounds according to the present invention can be effective at an amount of from about 0.01 μg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 μg to about 2000 mg, preferably from about 5 μg to about 1000 mg. In the case of combination therapy, a therapeutically effective amount of one or more other anticancer compounds can be administered in a separate pharmaceutical composition, or alternatively included in the pharmaceutical composition according to the present invention which contains a compound according to the present invention. The pharmacology and toxicology of many of such other anticancer compounds are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In the pharmaceutical compositions, the active agents can be in any pharmaceutically acceptable salt form. As used herein, the term "pharmaceutically acceptable salts" refers to the relatively non-toxic, organic or inorganic salts of the active compounds, including inorganic or organic acid addition salts of the compound.

For oral delivery, the active compounds can be incorporated into a formulation that includes pharmaceutically acceptable carriers such as binders, lubricants, disintegrating agents, and sweetening or flavoring agents, all known in the art. The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and anti-oxidants can all be included. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. A special form of topical administration is delivery by a transdermal patch. Methods for preparing transdermal patches are disclosed, e.g., in Brown, et al., *Annual Review of Medicine*, 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. See, e.g., Phillips et al., *J. Pharmaceut. Sci.*, 73:1718-1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.*, 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology*, Volume XIV, Academic Press, New York, N.Y. (1976).

The active compounds can also be administered in combination with another active agent that synergistically treats or prevents the same symptoms or is effective for another disease or symptom in the patient treated, so long as the other active agent does not interfere with, or adversely affect, the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

4. Therapeutic Methods

As used herein, the phrase "treating . . . with . . . a compound" means either administering the compound to cells or an animal, or administering to cells or an animal another agent to cause the presence or formation of the compound inside the cells or the animal. Preferably, the methods of the present invention comprise administering to cells in vitro or to a warm-blood animal, particularly mammal, and more particularly a human, a pharmaceutical composition comprising an effective amount of a compound according to the present invention.

The present invention provides therapeutic methods comprising treating an animal (e.g., a patient, in need of such treatment) a therapeutically effective amount of one or more compounds of Formulae I through VI, as defined above, and/or a pharmaceutically acceptable salt thereof. The therapeutic methods are particularly useful in the treatment of Hsp90 inhibitor-sensitive cancers, which comprise a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In another aspect, the invention provides a method of treating an Hsp90 inhibitor-sensitive cancer comprising administering to a patient in need of such treatment a therapeutically effective amount of a compound according to Formula I or II as defined above. In certain embodiments, this aspect further comprises identifying a patient having an Hsp90 inhibitor-sensitive cancer. In these certain embodiments, the identifying step may occur prior to the administering step.

In another aspect, the invention provides a method for treating an individual having an Hsp90 inhibitor-sensitive disease or disorder chosen from inflammatory diseases, infections, autoimmune disorders, stroke, ischemia, cardiac disorders, neurological disorders, proliferative disorders, neoplasms, malignant diseases, and metabolic diseases.

In yet another aspect, the invention provides a method for treating an individual having an Hsp90 inhibitor-sensitive fibrogenetic disorder, such as, for example, scleroderma, polymyositis, systemic lupus, rheumatoid arthritis, liver cirrhosis, keloid formation, interstitial nephritis and pulmonary fibrosis.

5. Methods of Making

The present invention provides methods of making compounds having a structure according to Formula I or II as defined above. The methods comprise following the procedures of one of Reaction Schemes 1 through 5 disclosed below.

EXAMPLES

Chemical Synthesis and Purification of Example Compounds

All reactions were performed in flame-dried or oven-dried glassware under a positive pressure of dry nitrogen or dry argon and were stirred magnetically unless otherwise indicated. Chemicals were purchased from standard commercial vendors and used as received unless otherwise noted. Any necessary preparations not referenced or described herein were facile and known to one of ordinary skill in the art. Yields are not optimized. The chemical names were mostly generated using the ACD labs software (Version 8.08) available from Advanced Chemistry Development, Inc. (Toronto, Ontario, Canada), or the "Autonom 2000" plug-in for the Isis™/Draw 2.5SP1 chemical drawing program, available from MDL Information Systems, a division of Symyx technologies, Inc. (Santa Clara, Calif.).

Analytical TLC plates (Silica Gel 60 F254, EM Science, Merck 5715-7, EM Science, Gibbstown, N.J.) were used to follow the course of reactions, and the MPLC system used for purifications (Isco Foxy Jr fraction collector, UA-6 detector) was from Teledyne Isco, Inc. (Lincoln, Nebr.), using Isco silica gel flash columns. $^1$H NMR spectra were recorded on a Varian Mercury 400 MHz instrument (Varian Inc., Polo Alto, Calif.) and chemical shifts are expressed in parts per million (ppm, δ) relative to TMS as the internal standard. Mass spectra were obtained on an Agilent LC/MS TOF, injection volume 2 uL, XTerra MS-$C_{18}$ 3.5 μm 2.1×50 mm column (Agilent Technologies, Santa Clara, Calif.) ESI source. Analytical HPLC was performed on an HP1100 (Agilent Technologies, Santa Clara, Calif.) injection volume 5 μl, Waters (Waters Corporation, Milford, Mass.) XBridge $C_{18}$ 5 μm 4.6×150 mm column. Preparative HPLC purifications were performed using Agilent HP-1100 preparative LC. Samples were dissolved in dimethylsulfoxide and injected on Waters XTera prep MS $C_{18}$ (Waters Corporation, Milford, Mass.) 19×250 mm, 10μ particles were used. The column was eluted with a mixture of acetonitrile and water (both containing 0.01% v/v trifluoroacetic acid) in a flow rate of 30 mL/min and a gradient of 25% to 100% methanol over a period of 20 min.

Abbreviations and Acronyms

When the following abbreviations are used herein, they have the following meaning:

| | |
|---|---|
| $Ac_2O$ | acetic anhydride |
| anhy | Anhydrous |
| n-BuOH | n-butanol |
| t-BuOH | t-butanol |
| $CD_3OD$ | methanol-$d_4$ |
| Celite ® | diatomaceous earth filter agent, ® Celite Corp. |
| $CH_2Cl_2$ | methylene chloride |
| DCM | dichloromethane |
| CI-MS | chemical ionization mass spectroscopy |
| conc | concentrated |
| dec | decomposition |
| bs | broad singlet |
| br | broad |
| DME | dimethoxyethane |
| DMF | N, N-dimethylformamide |
| DMSO | dimethylsulfoxide |
| DMSO-$d_6$ | dimethylsulfoxide-$d_6$ |
| ELSD | evaporative light scattering device |
| EtOAc | ethyl acetate |
| EtOH | ethanol (100%) |
| $Et_2O$ | diethyl ether |
| $Et_3N$ | triethylamine |
| HPLC ESI-MS | high performance liquid chromatography-electrospray mass spectroscopy |
| MPLC | medium pressure liquid chromatography |
| NMR | nuclear magnetic resonance spectroscopy |
| TOF-MS | time-of-flight-mass spectroscopy |
| NMM | 4-methylmorpholine |
| $Ph_3P$ | triphenylphosphine |
| Pd(dppf)$Cl_2$ | [1,1'-bis(diphenylphosphino)ferrocene]dichloropalladium(II) |

| | |
|---|---|
| Pd(PPh₃)₄ | tetrakis(triphenylphosphine)palladium(0) |
| Pd(OAc)₂ | palladium(II) acetate |
| P(O)Cl₃ | phosphorous oxychloride |
| $R_f$ | TLC retention factor |
| RT | retention time (HPLC) |
| rt | room temperature |
| THF | tetrahydrofuran |
| TFA | trifluoroacetic acid |
| TLC | thin layer chromatography |
| LC-MS (ESI) | liquid chromatography-mass spectroscopy (electrospray ionization) |
| DIEA | diisopropylethylamine |
| TFAA | trifluoroacetic anhydride |
| MsCl | methanesulfonylchloride |
| AcOH | acetic acid |
| HCl | hydrochloric acid |
| $H_2SO_4$ | sulfuric acid |
| $HNO_3$ | nitric acid |
| HBr | hydrobromic acid |
| $CDCl_3$ | chloroform-$d_3$ |
| $CHCl_3$ | chloroform |
| $H_2O$ | water |
| NaOAc | sodium acetate |
| KOH | potassium hydroxide |
| NaOH | sodium hydroxide |
| NaCl | sodium chloride |
| $NaHCO_3$ | sodium bicarbonate |
| $Na_2CO_3$ | sodium carbonate |
| $K_2CO_3$ | potassium carbonate |
| $Na_2SO_4$ | sodium sulfate |
| $MgSO_4$ | magnesium sulfate |
| MeOH | methanol |
| $SiO_2$ | silica gel |
| $K_3PO_4$ | potassium phosphate |
| $NH_4Cl$ | ammonium chloride |
| AIBN | 2,2'-axo bisisobutyronitrile |
| Barton's base | 2-t-butyl-1,1,3,3-tetramethylguanidine |
| DMAP | N,N-Dimethyl aminopyridine |
| LG | leaving group |
| MsCl | methanesulfonyl chloride |
| TsCl | p-toluenesulfonyl chloride |
| PG | protecting group |
| Xantphos | 4,5-bis(diphenylphosphino)-9,9-dimethyl xanthane |
| TBAH | Tetra butyl ammonium hydroxide |

Methods of Synthesis

General methods, according to some embodiments, for the preparation of the compounds of the present invention are provided below.

Reaction Scheme 1:

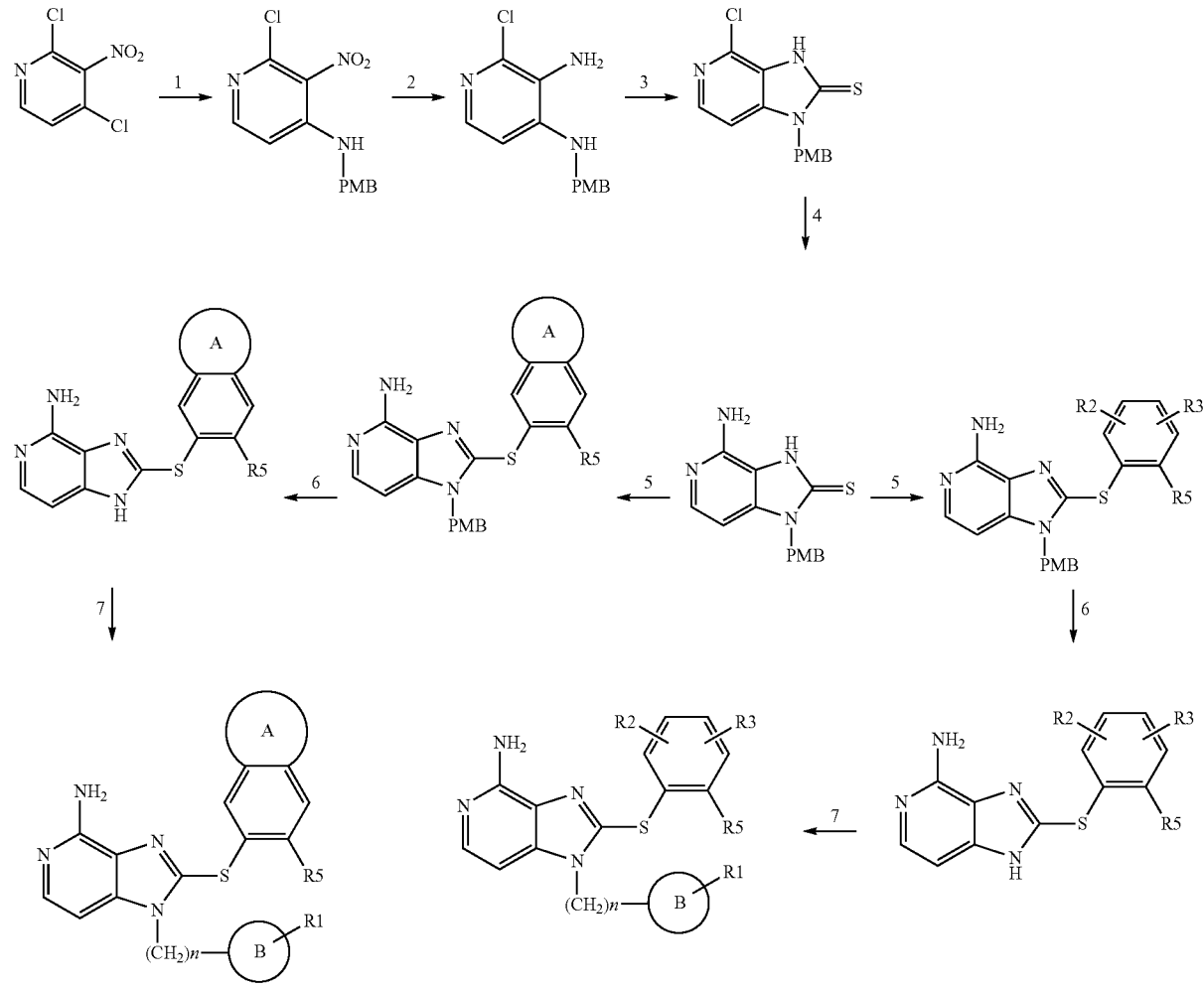

Reagents: 1) H₂NPMB, 2) Fe/HCl, 3) CS₂, KOH, 4) NaNH₂, NH₃, 5) Ar—Y (Y=I, Br), NaOtBu, neocuproine, CuI, or pd₂dba₃, Xantphos, Cs₂CO₃, dioxane, 6) CF3COOH, and 7)
Reagents: 1) Formic acid, 2) POCl₃, 3) NaNH₂, NH₃, 4) Bromine or t-Butyl Hypochlorite, 5) Ar—SH, 6)
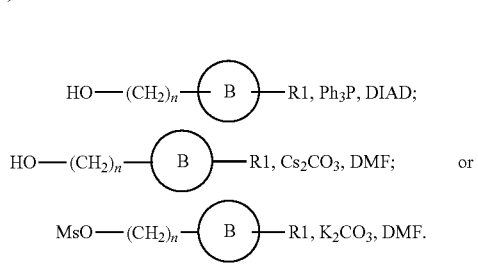
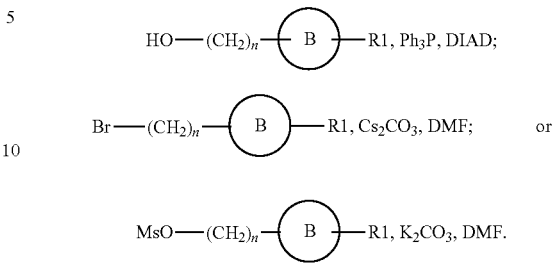
Reaction Scheme 2:
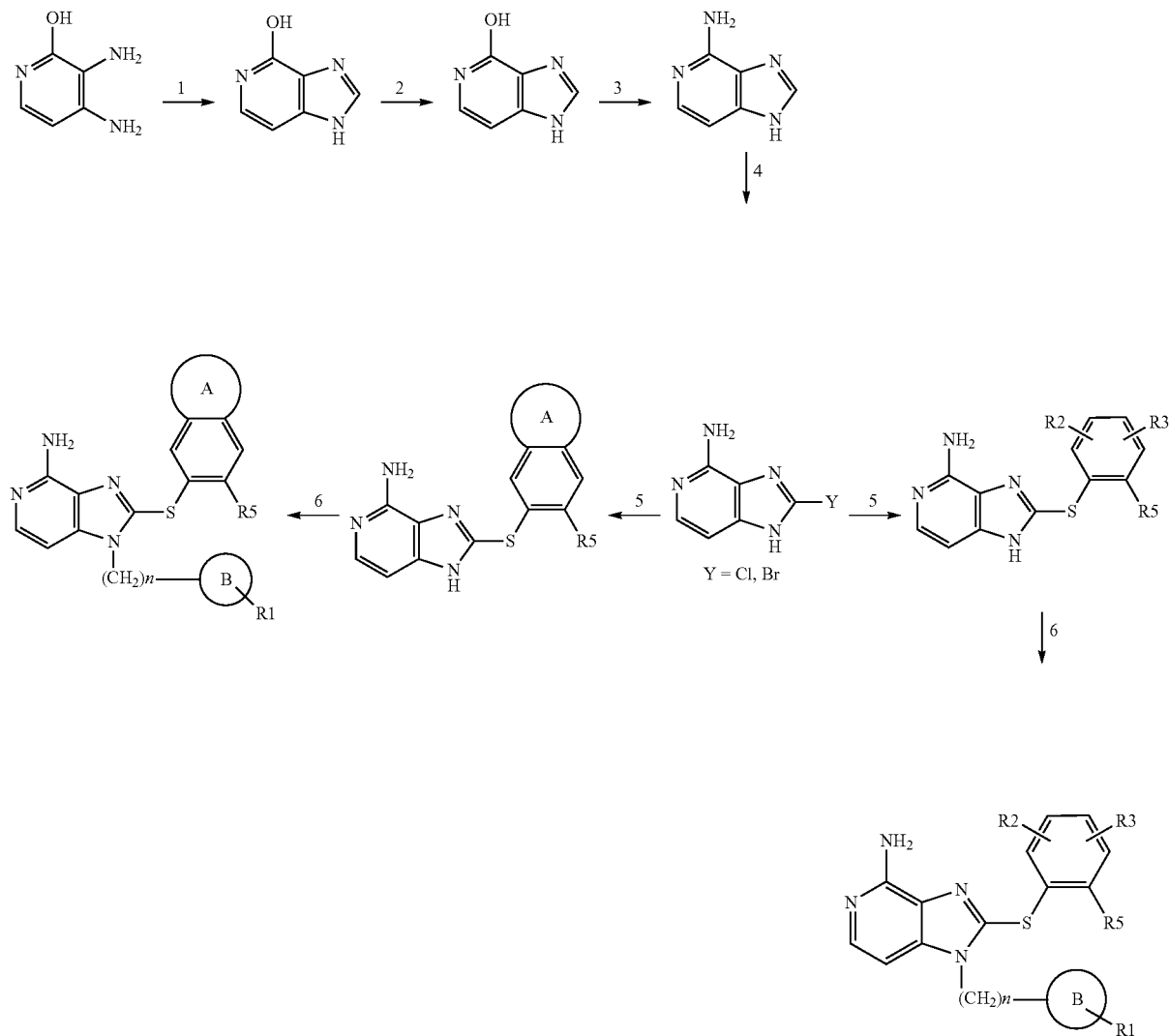

Reaction Scheme 3:

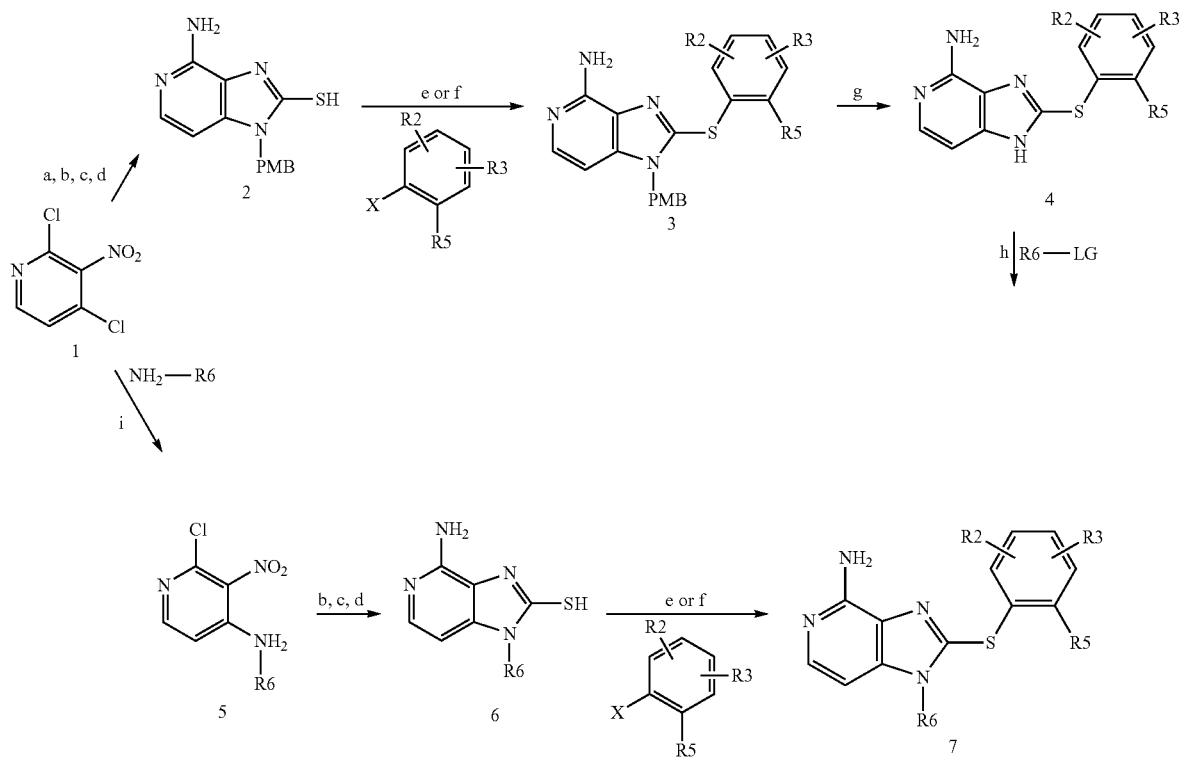

Reagents and conditions: a) p-methoxybenzylamine, NEt$_3$, DMF; b) Fe, acetic acid; c) CS$_2$, KOH, EtOH; d) liquid NH$_3$, NaNH$_2$; e) CuI, neocuproine, NaOtBu, DMF, 100° C.; f) Pd$_2$dba$_3$, Xantphos, Cs$_2$CO$_3$, dioxane, 100° C.; g) TFA, 80° C.; h) R4-LG, base (K$_2$CO$_3$, Cs$_2$CO$_3$), DMF, 25° C.-100° C.; i) NH$_2$—R4, NEt$_3$, DMF.

In Reaction Scheme 3, R6 represents

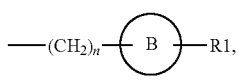

wherein n, B, and R1 are as defined above for Formula II. LG represents any leaving group compatible with R6. Examples of LG include acetate (AcO), p-nitrobenzoate (PNBO), sulfonates (e.g., methanesulfonate (Mesylate: MsO), p-toluenesulfonate (tosylate: TsO), p-bromobenzenesulfonate (Brosylate: BsO), p-nitrobenzenesulfonate (Nosylate: NsO), fluoromethanesulfonate, difluoromethanesulfonate, trifluoromethanesulfonate (Triflate: TfO) and ethanesulfonate), and halogens (e.g., I, Br, and Cl). X represents halo. R2, R3, and R5 are as defined above for Formula II. The target compounds 7 may be synthesized by either approach of Reaction Scheme 3. The first approach involves the synthesis of PMB protected compound 2, which requires a standard four-step procedures (i. SnAr reaction with 1-(4-methoxyphenyl)methanamine; ii. reduction of 3-nitro group; iii. imidazole ring formation by treatment with carbon disulfide; iv. displacement of 2-chlorine with sodium amide). Compound 3 may be obtained by a copper or palladium catalyzed coupling of aryl iodides or aryl bromides with 2. Deprotection of the PMB group in 3 provides key intermediates 4 bearing a free NH and subsequent alkylation of 4 with alkylating agents (R6-LG) affords target compounds 7. The second approach begins with SnAr reaction of 2,4-dichloro-3-nitropyridine 1 with substituted amines to provide 5. Using 5 the remaining 4 steps are followed in a manner analogous first approach to obtain target compounds 7. In either approach, R6 may be protected with a protecting group such as, for example, Boc, that may be deprotected to provide the R1 substituent of R6. Additionally, R6 encompasses intermediates that may be transformed by standard methods to generate

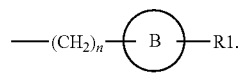

For example, regarding R6, in place of the substituent R1 may be an intermediate that may be later transformed to provide R1.

Reaction Scheme 4:

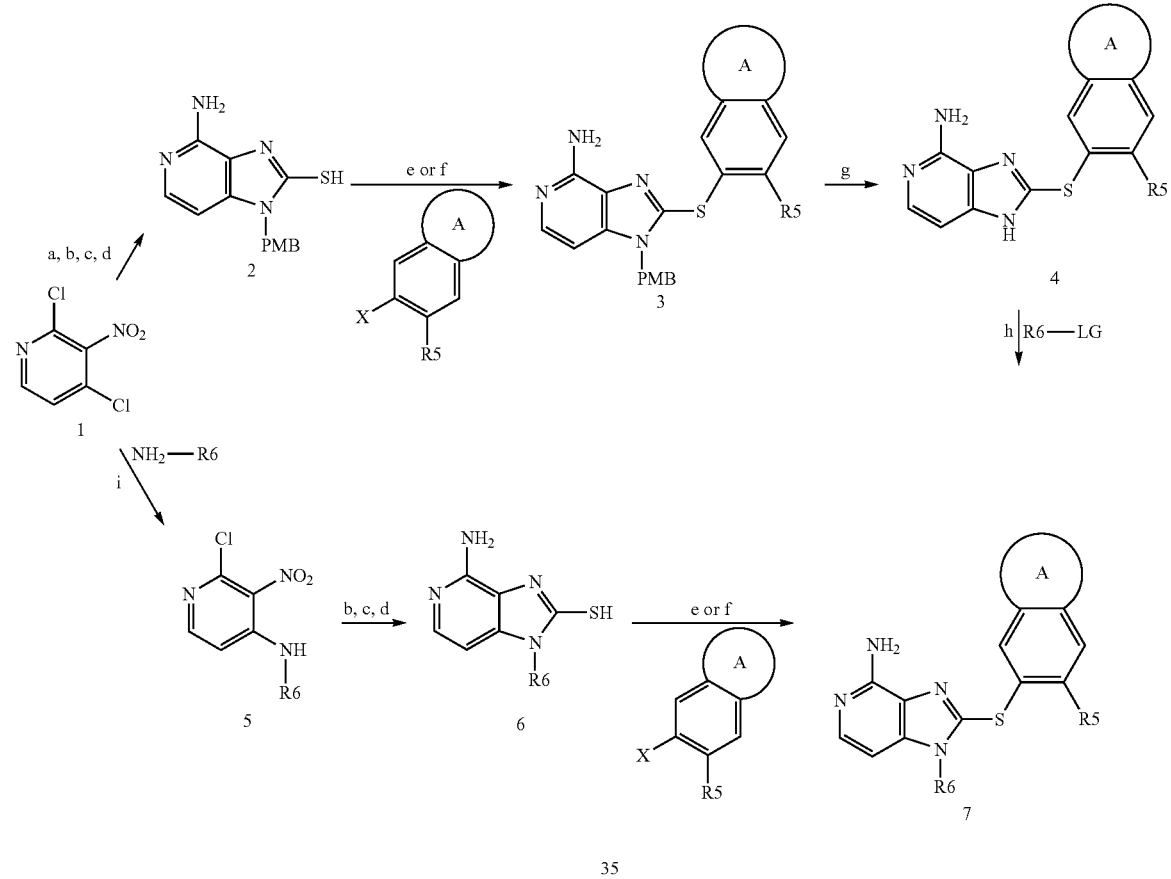

Reagents and conditions: a) p-methoxybenzylamine, NEt$_3$, DMF; b) Fe, acetic acid; c) CS$_2$, KOH, EtOH; d) liquid NH$_3$, NaNH$_2$; e) CuI, neocuproine, NaOtBu, DMF, 100° C.; f) Pd$_2$dba$_3$, Xantphos, Cs$_2$CO$_3$, dioxane, 100° C.; g) TFA, 80° C.; h) R4-LG, base (K$_2$CO$_3$, Cs$_2$CO$_3$), DMF, 25° C.-100° C.; i) NH$_2$—R4, NEt$_3$, DMF.

In Reaction Scheme 4, R6 represents

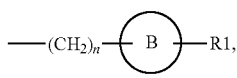

wherein n, B, and R1 are as defined above for Formula I. LG represents any leaving group compatible with R6. Examples of LG include acetate (AcO), p-nitrobenzoate (PNBO), sulfonates (e.g., methanesulfonate (Mesylate: MsO), p-toluenesulfonate (tosylate: TsO), p-bromobenzenesulfonate (Brosylate: BsO), p-nitrobenzenesulfonate (Nosylate: NsO), fluoromethanesulfonate, difluoromethanesulfonate, trifluoromethanesulfonate (Triflate: TfO) and ethanesulfonate), and halogens (e.g., I, Br, and Cl). X represents halo. R5 is as defined above for Formula I. The target compounds 7 may be synthesized by either approach of Reaction Scheme 4. The first approach involves the synthesis of PMB protected compound 2, which requires a standard four-step procedures (i. SnAr reaction with 1-(4-methoxyphenyl)methanamine; ii. reduction of 3-nitro group; iii. imidazole ring formation by treatment with carbon disulfide; iv. displacement of 2-chlorine with sodium amide). Compound 3 may be obtained by a copper or palladium catalyzed coupling of aryl iodides or aryl bromides with 2. Deprotection of the PMB group in 3 provides key intermediates 4 bearing a free NH and subsequent alkylation of 4 with alkylating agents (R6-LG) affords target compounds 7. The second approach begins with SnAr reaction of 2,4-dichloro-3-nitropyridine 1 with substituted amines to provide 5. Using 5, the remaining 4 steps are followed in a manner analogous first approach to obtain target compounds 7. In either approach, R6 may be protected with a protecting group such as, for example, Boc, that may be deprotected to provide the R1 substituent of R6. Additionally, R6 encompasses intermediates that may be transformed by standard methods to generate

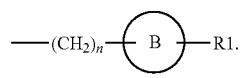

For example, regarding R6, in place of the substituent R1 may be an intermediate that may be later transformed to provide R1.

Regarding Reaction Schemes 1-4, in addition that disclosed above, methods of attaching and/or transforming R6, or its equivalent in Reaction Schemes 1 and 2, are disclosed in U.S. Pat. No. 7,595,401 and International Application Publication No. WO 2009/065035, which are incorporated by reference herein in their entirety.

Reaction Scheme 5 illustrates a method of making 4-(2-{4-amino-2-[(6-bromo-1,3-benzodioxol-5-yl)sulfanyl]-1H-imidazo[4,5-c]pyridin-1-yl}ethyl)piperidine-1-carbaldehyde, the final compound of example 1, according to some embodiments of the invention.

Reaction Scheme 5:

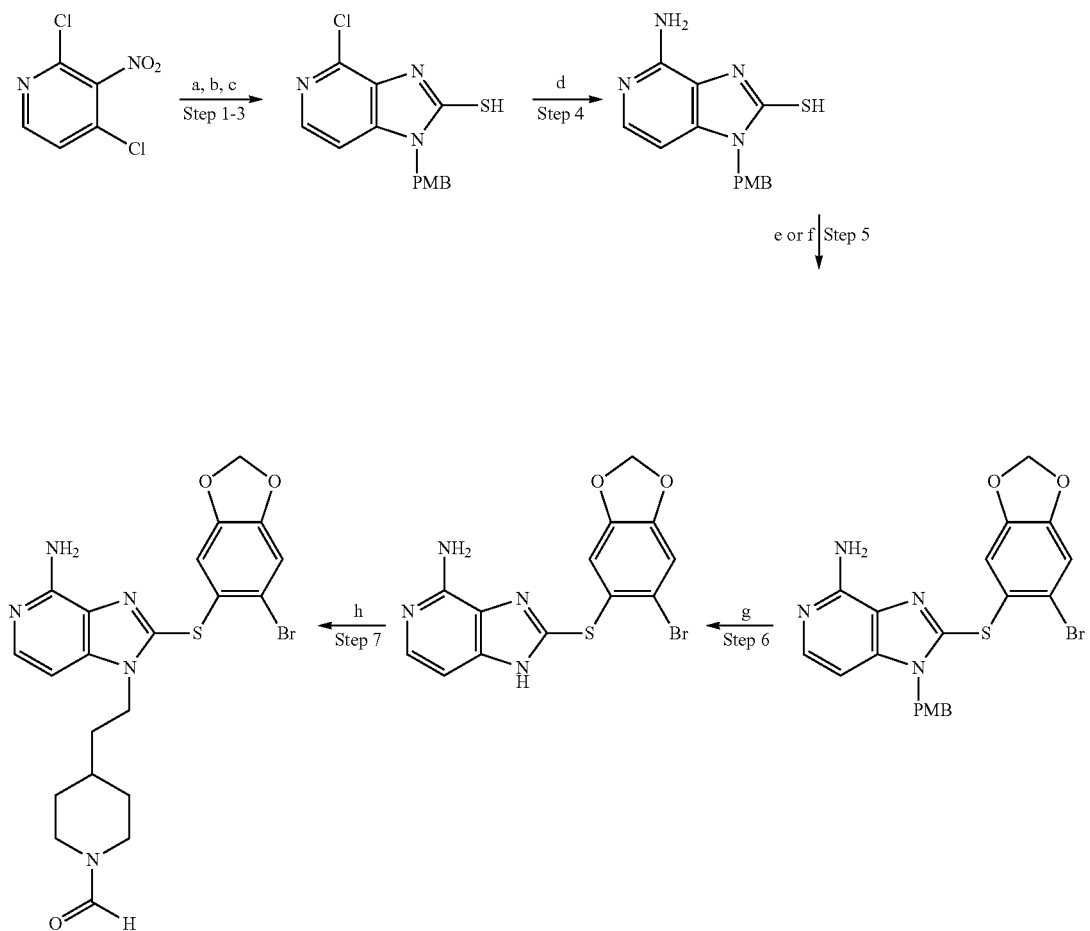

Reagents and conditions: a) p-methoxybenzylamine, NEt$_3$, DMF; b) Fe, acetic acid; c) CS$_2$, KOH, EtOH; d) NH$_3$ (1), NaNH$_2$; e) CuI, neocuproine, NaOtBu, 5-bromo-6-iodo-1,3-benzodioxole, DMF, 100° C.; f) Pd$_2$dba$_3$, Xantphos, Cs$_2$CO$_3$, 5,6-dibromo-1,3-benzodioxole, dioxane, 100° C.; g) TFA, 80° C.; h) 2-(1-formylpiperidin-4-yl)ethyl 4-methyl-benzenesulfonate, Cs$_2$CO$_3$, DMF, 85° C.

Exemplary Compounds of the Invention

Non-limiting examples of exemplary compounds of the present invention, which can be made using the Reaction Schemes above, are shown below.

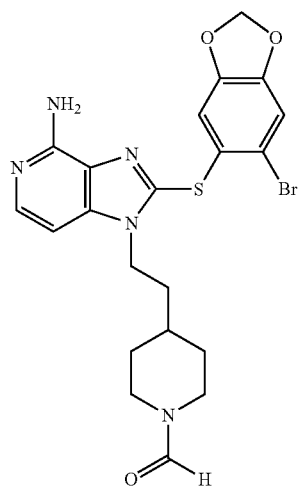

29
-continued
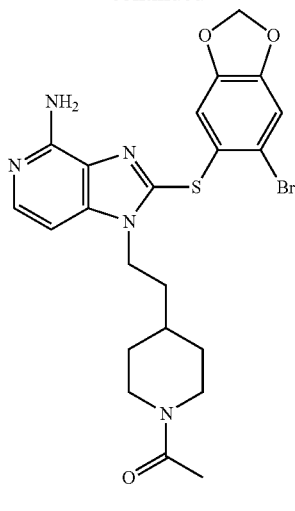
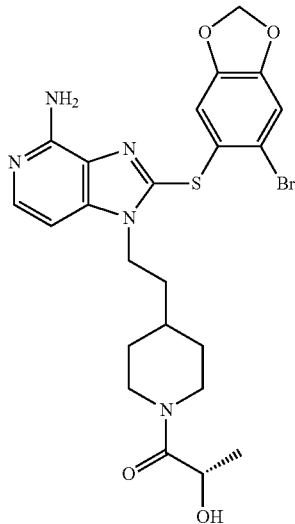
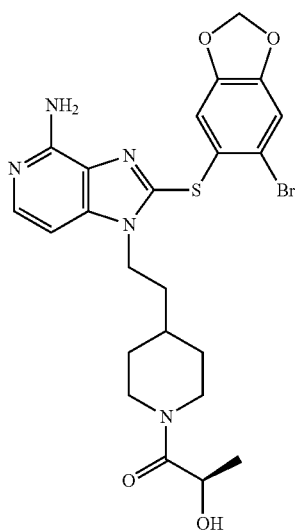
30
-continued
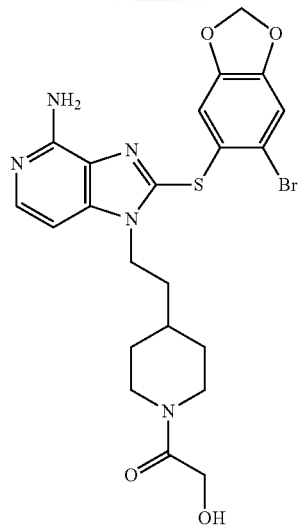
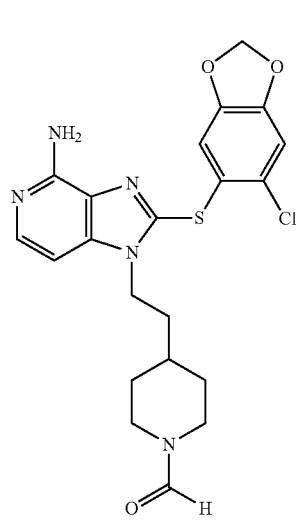
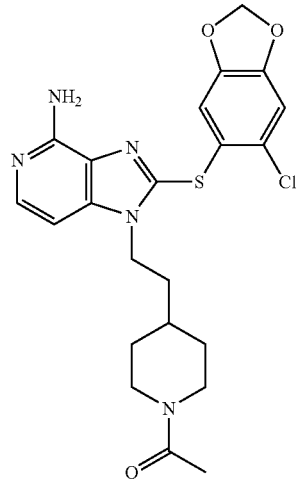

31
-continued
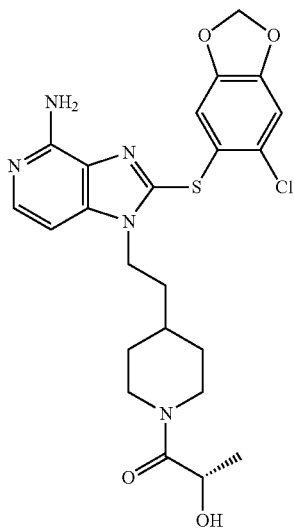
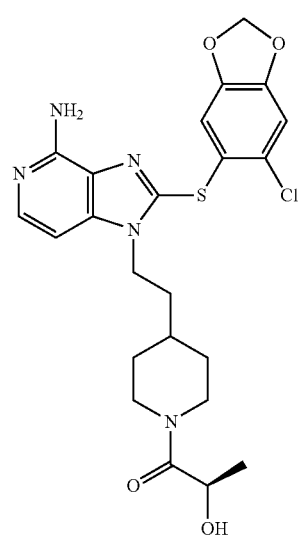
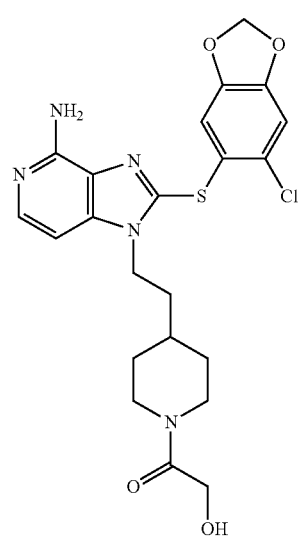
32
-continued
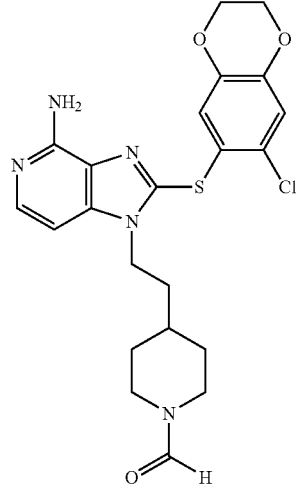
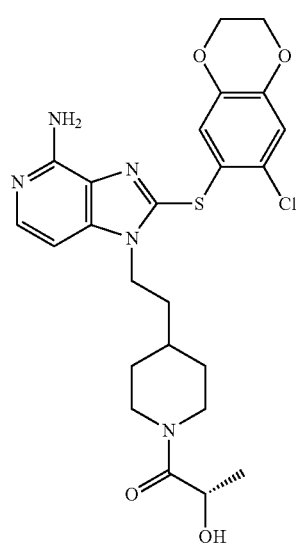

33
-continued
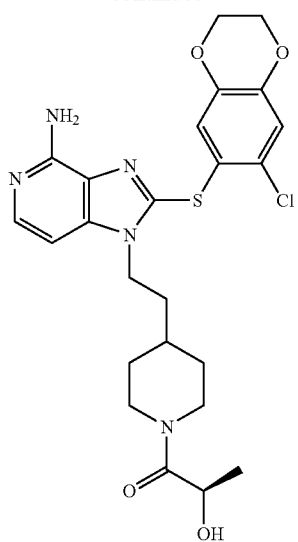
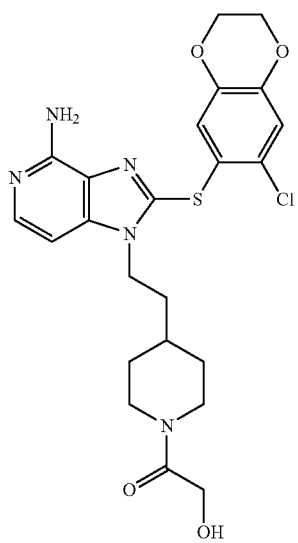
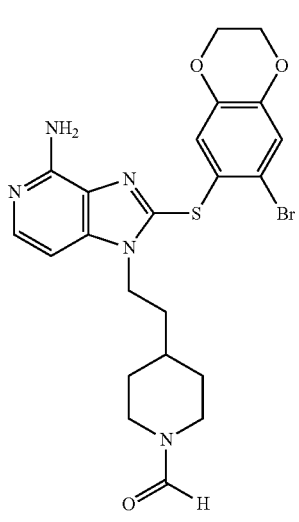
34
-continued
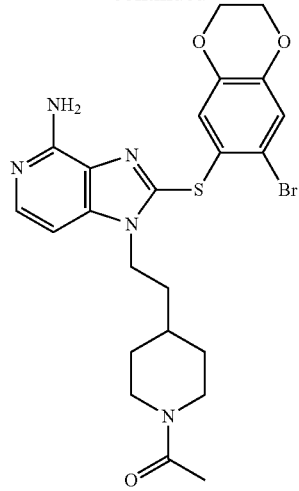
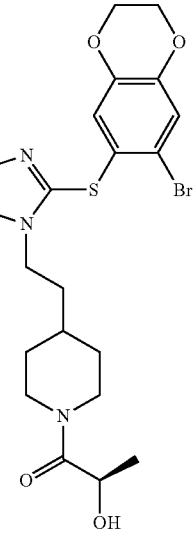

35
-continued
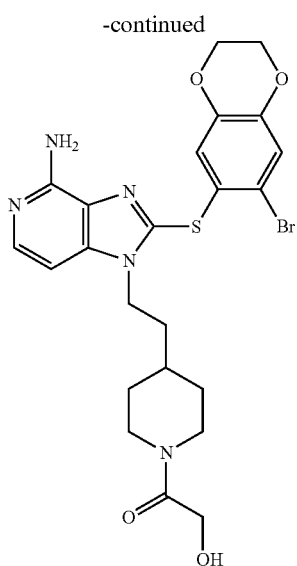
36
-continued
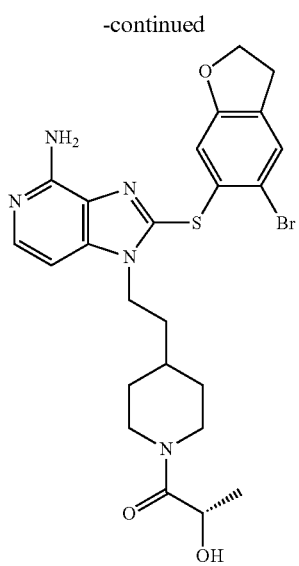
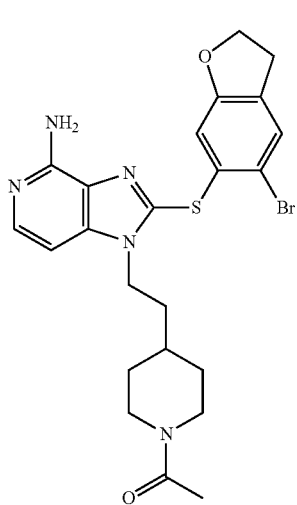
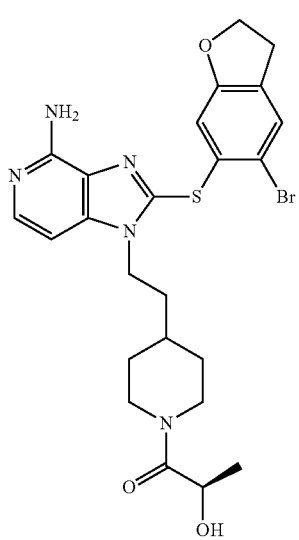
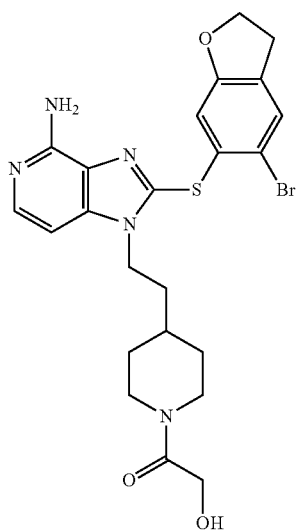

37
-continued
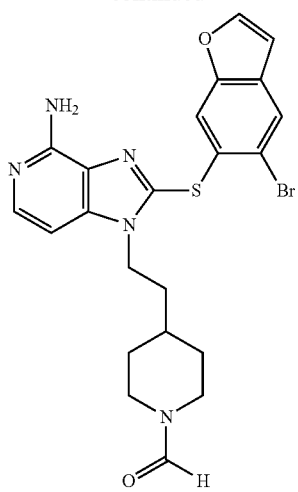
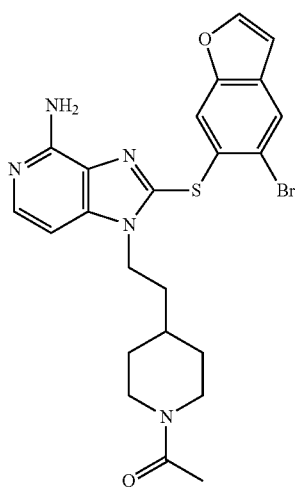
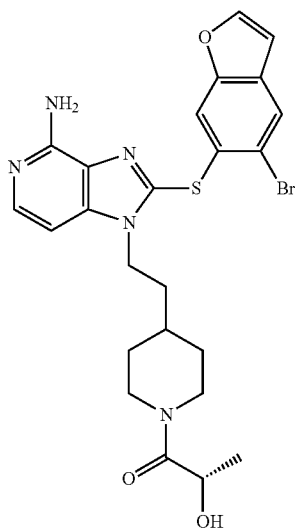
38
-continued
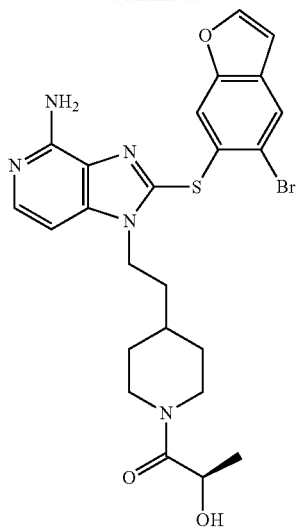
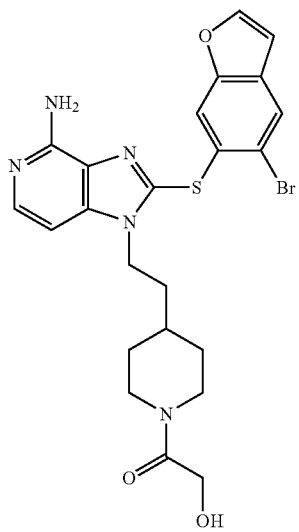
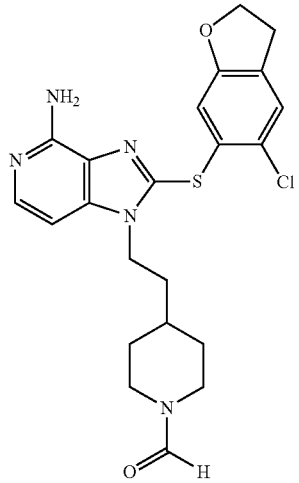

39
-continued
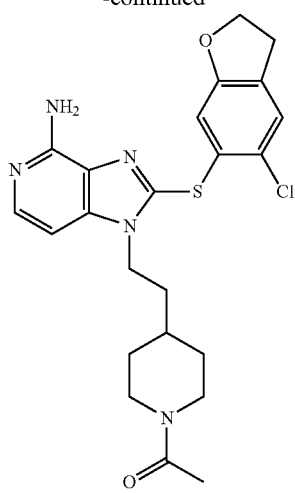
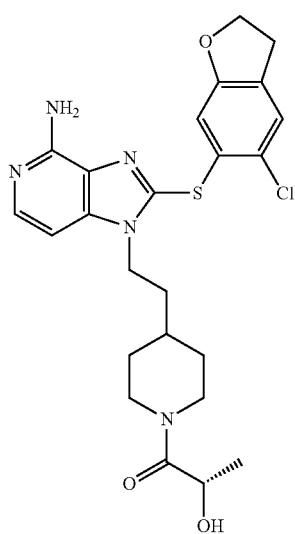
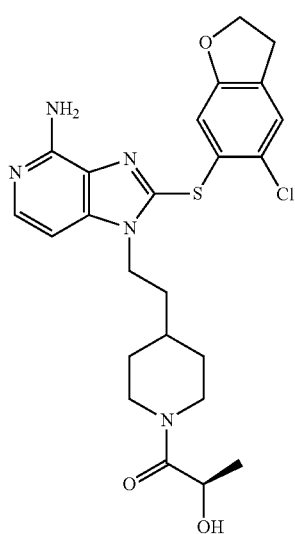
40
-continued
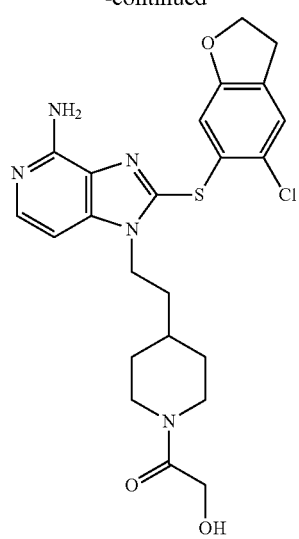
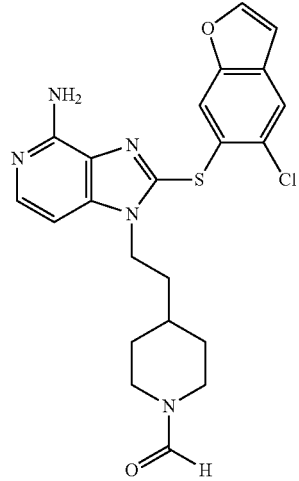
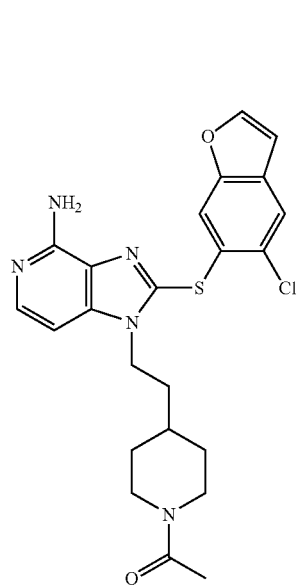

41
-continued
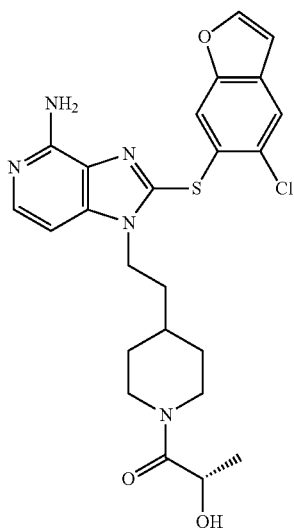
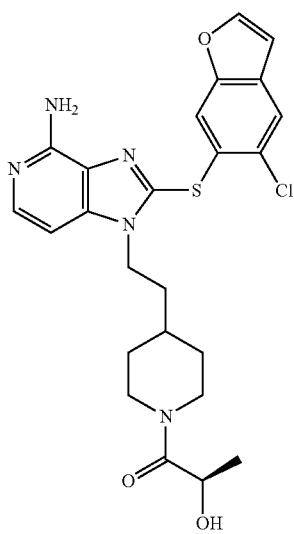
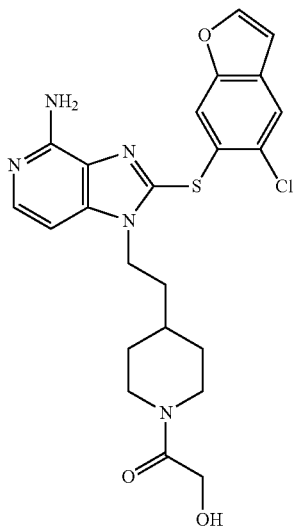
42
-continued
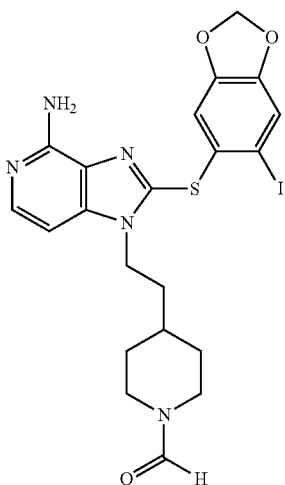
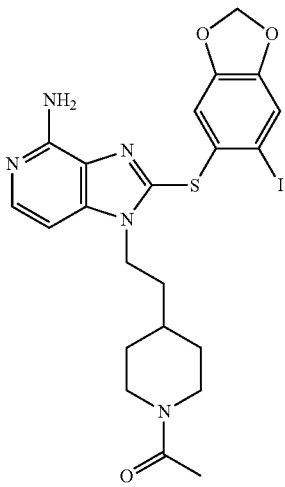
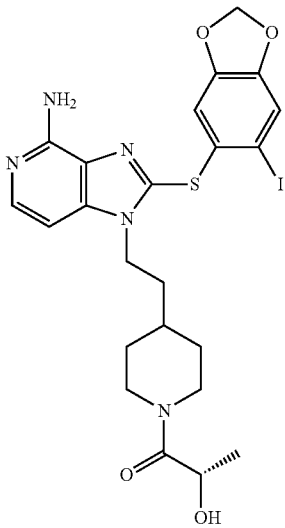

43
-continued
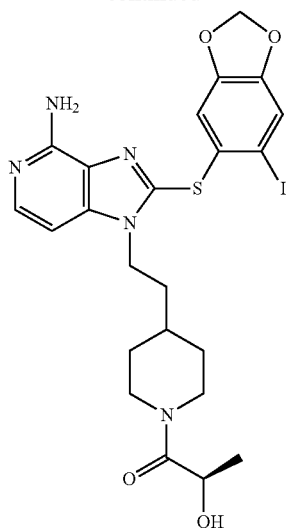
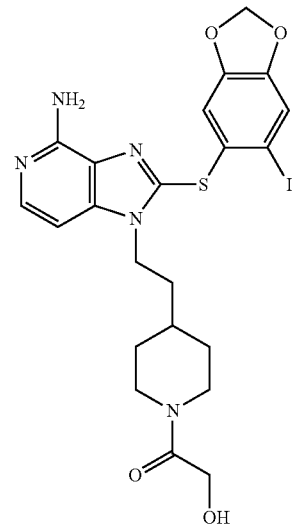
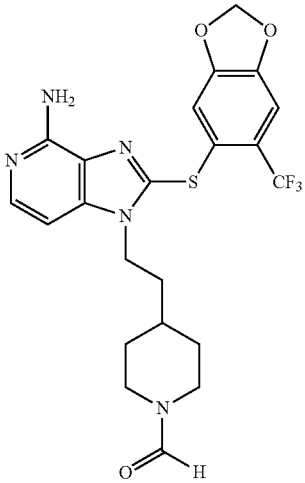
44
-continued
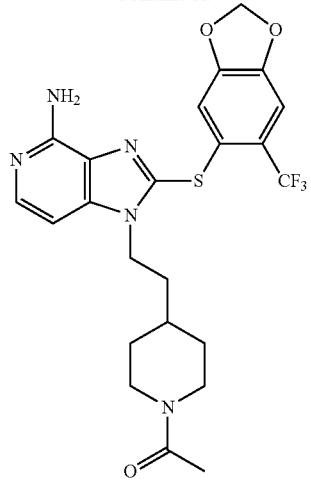
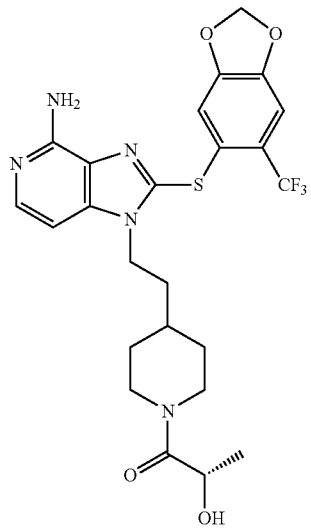
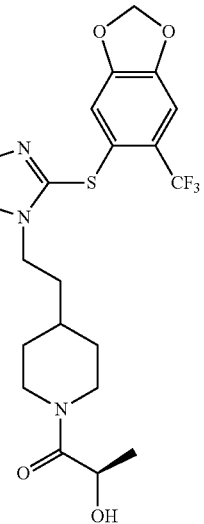

45
-continued
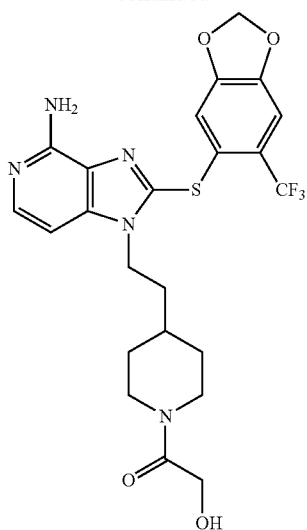
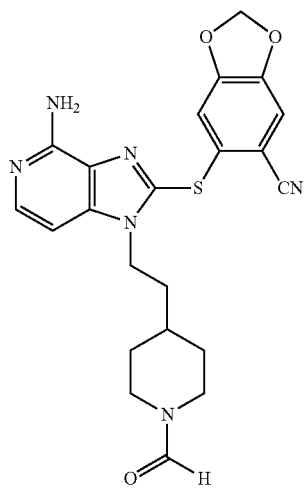
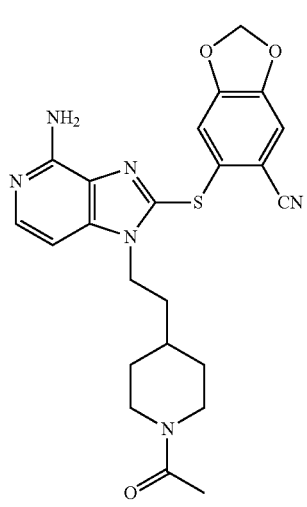
46
-continued
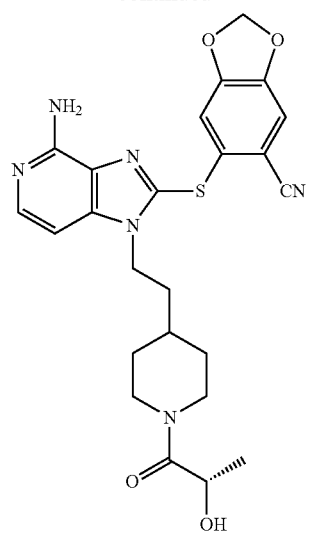
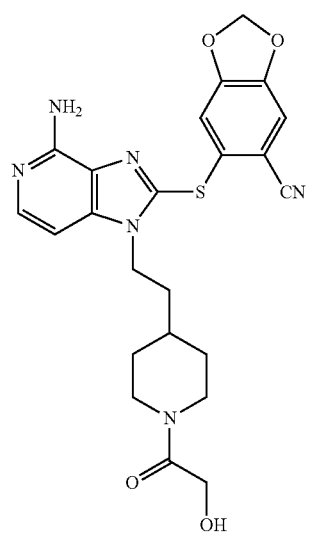

47
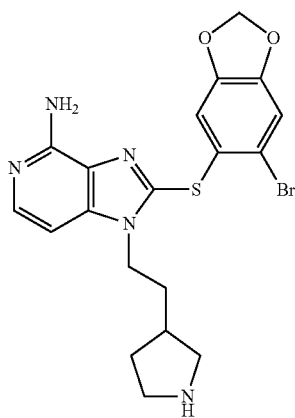
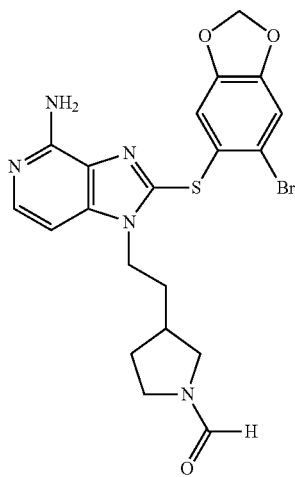
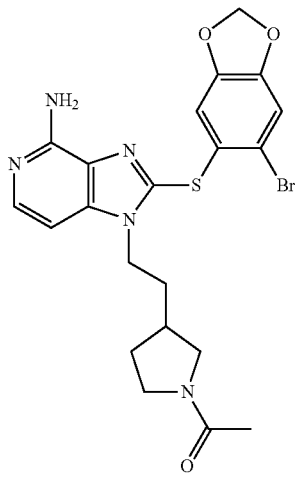
48
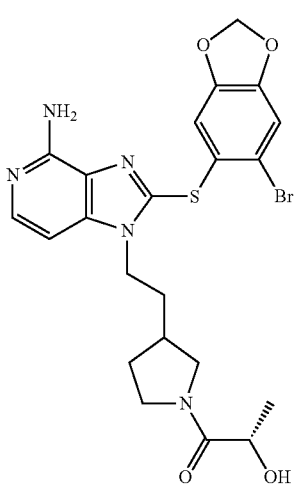
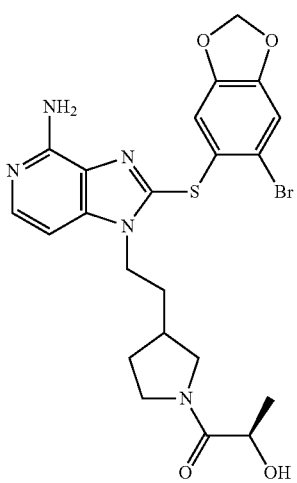
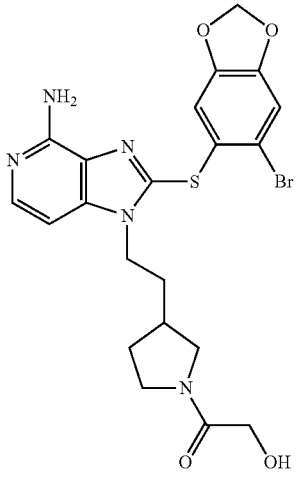

-continued
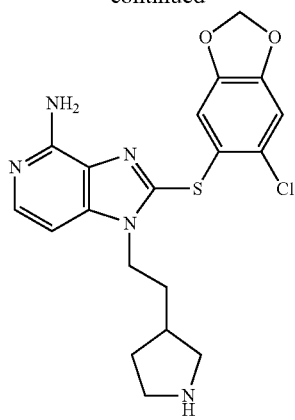
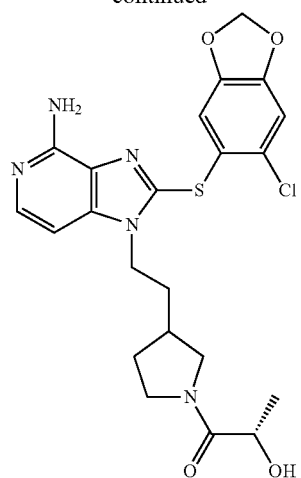
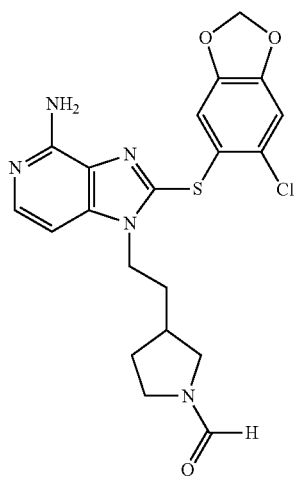
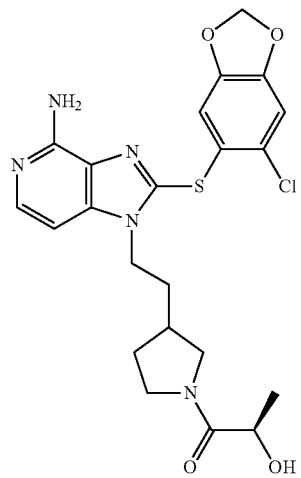
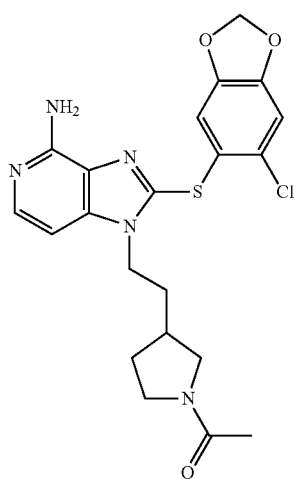
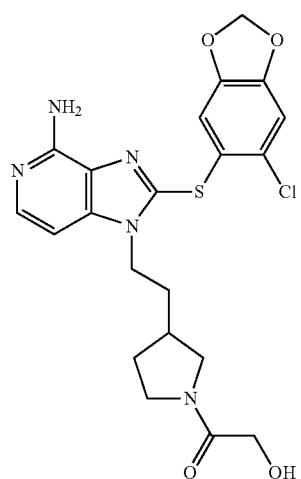

51
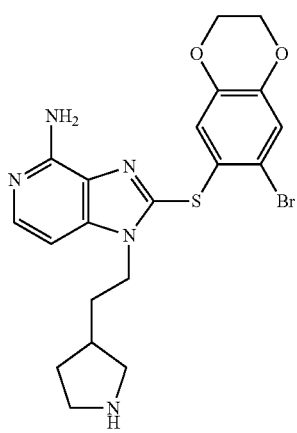
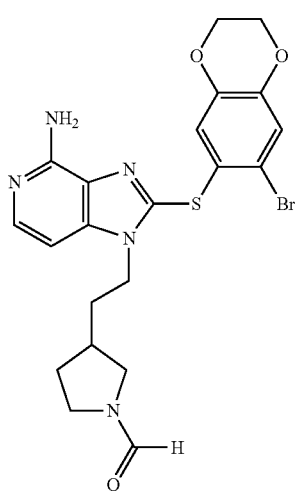
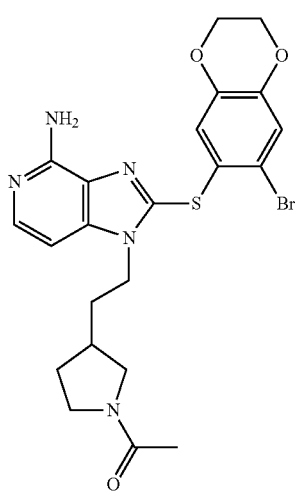
52
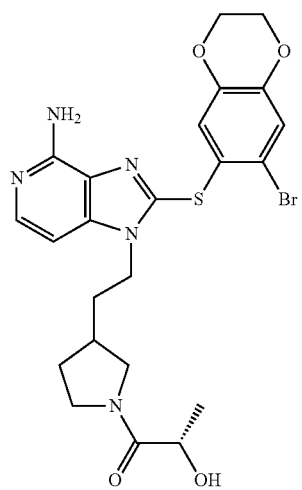
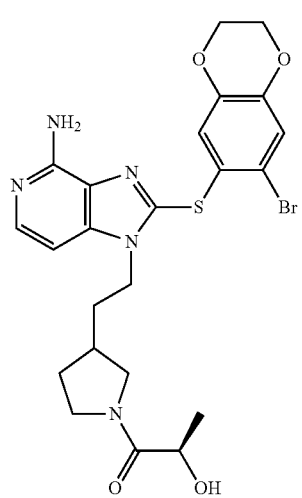
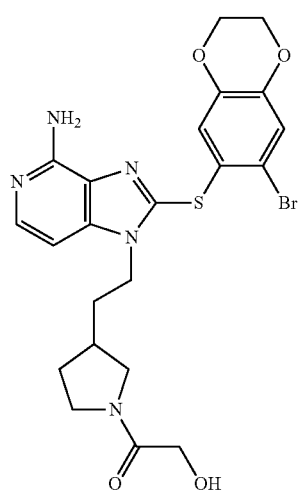

53
-continued
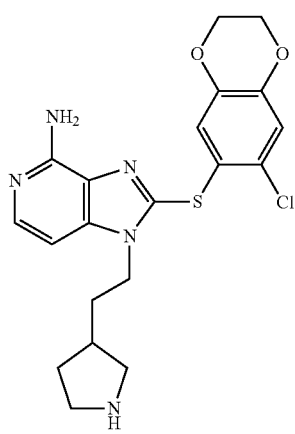
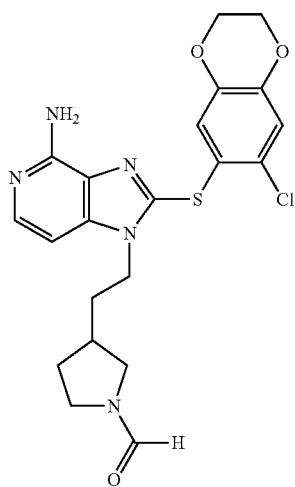
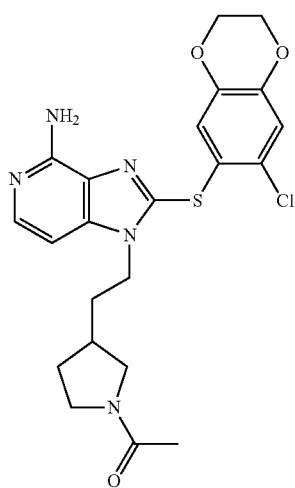
54
-continued
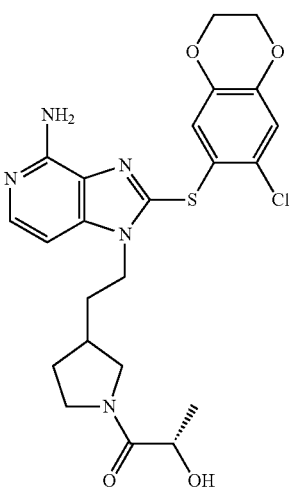
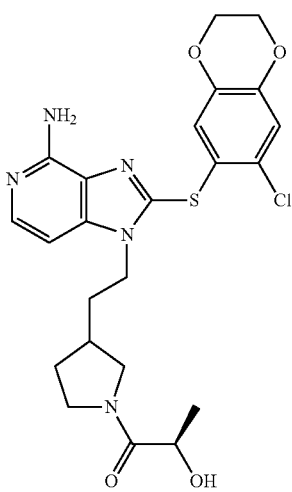
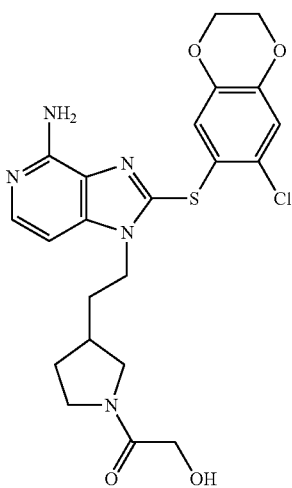

55
-continued
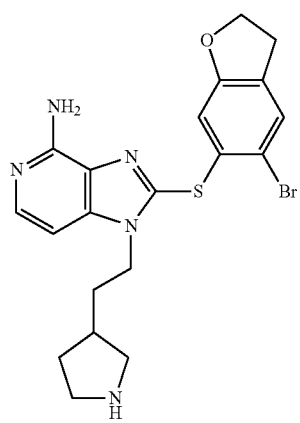
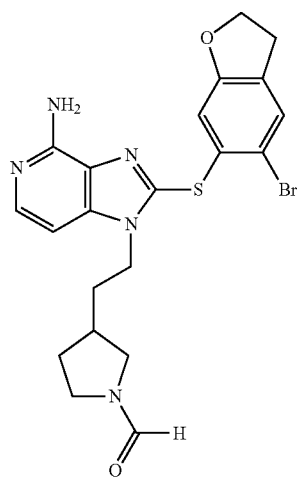
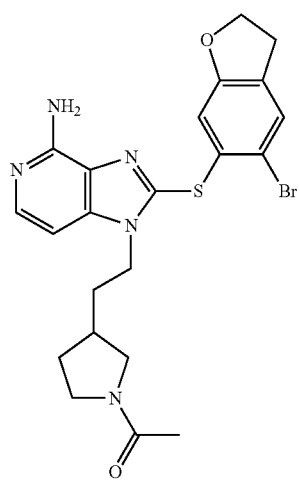
56
-continued
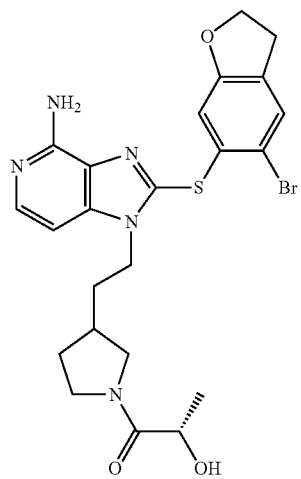
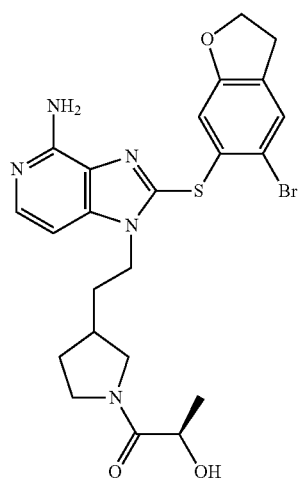
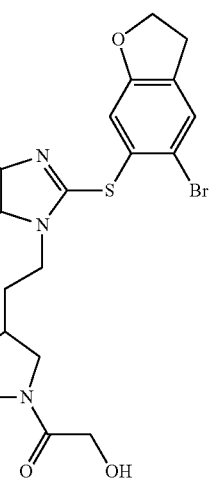

57
-continued
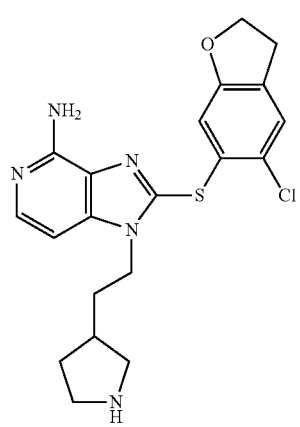
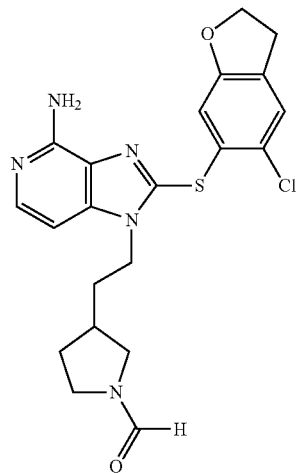
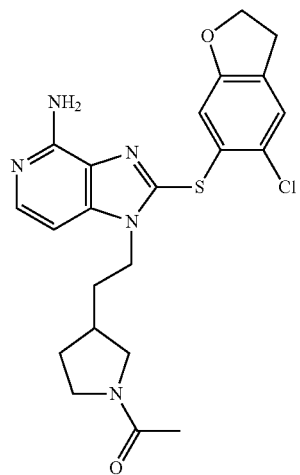
58
-continued
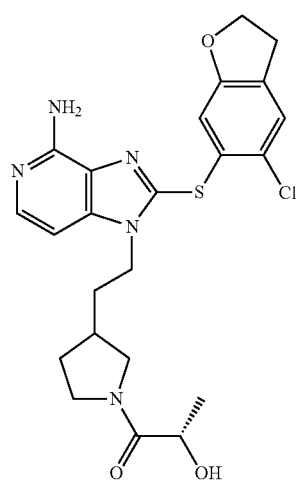
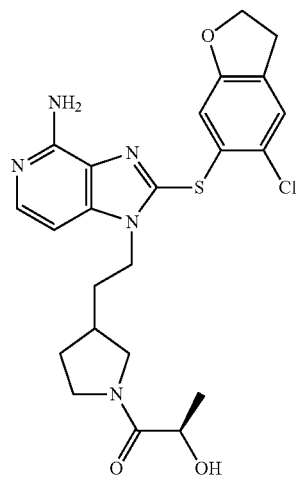
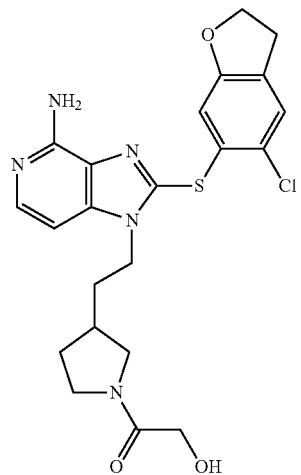

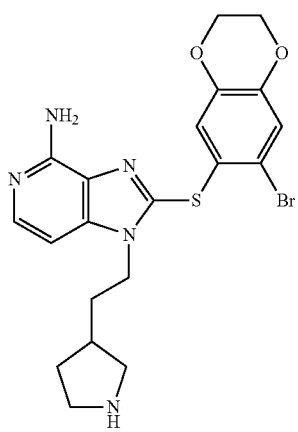
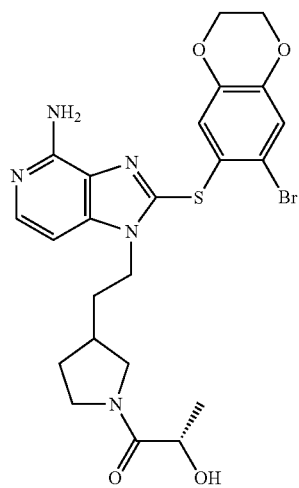
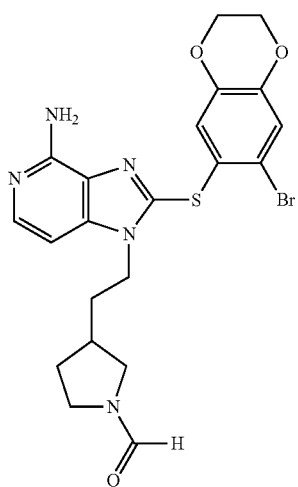
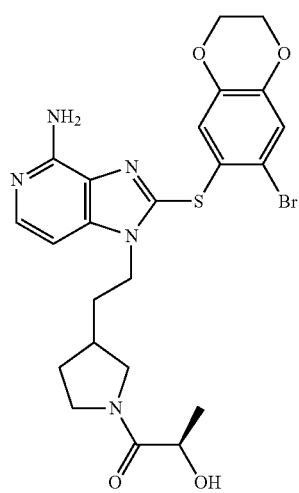
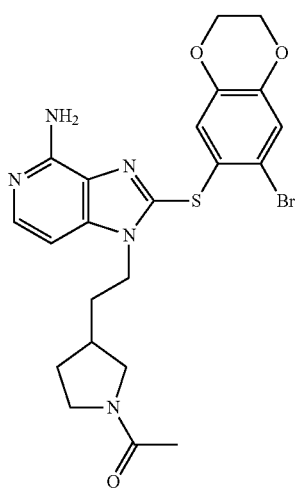
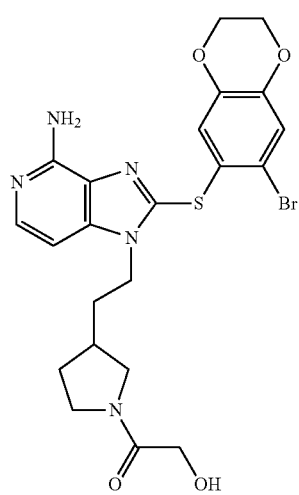

61
-continued
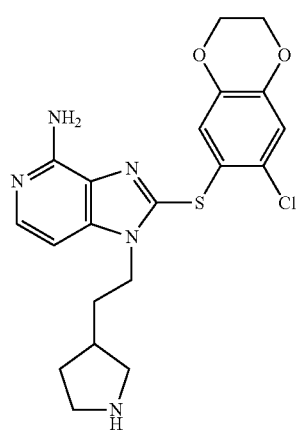
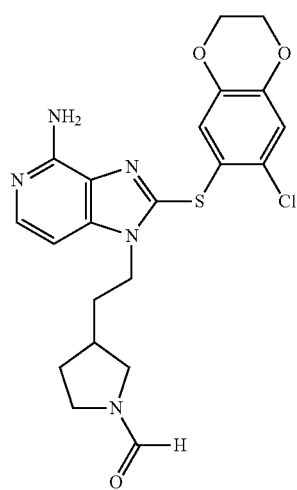
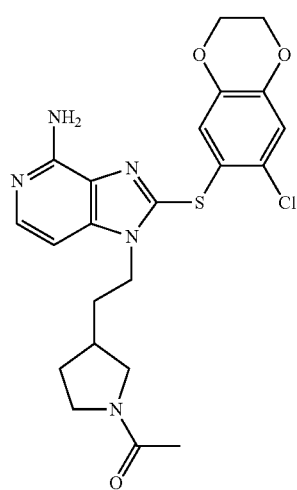
62
-continued
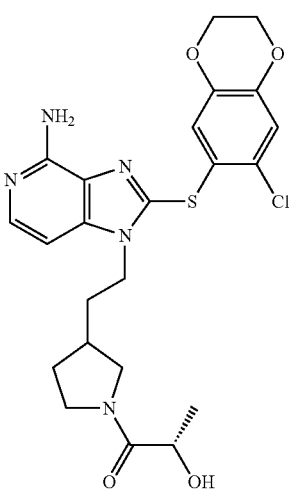
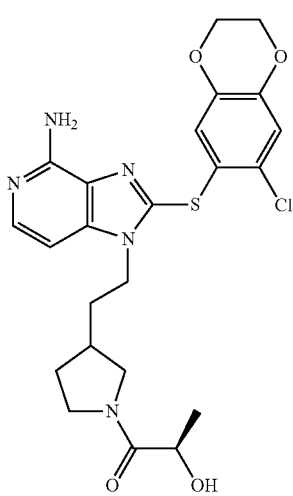
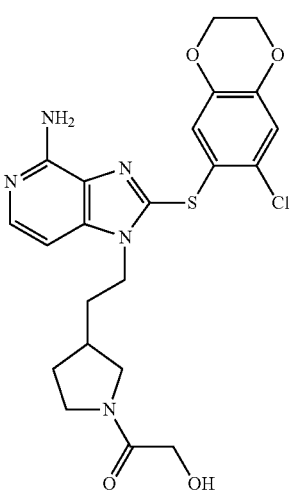

63
-continued
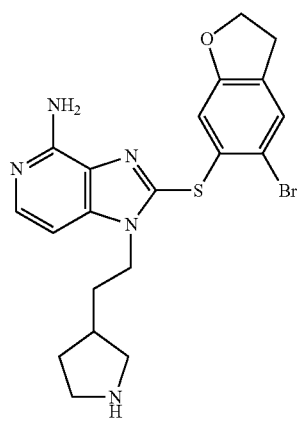
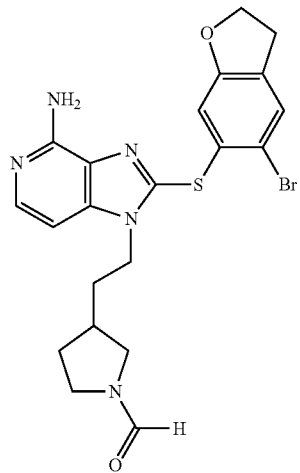
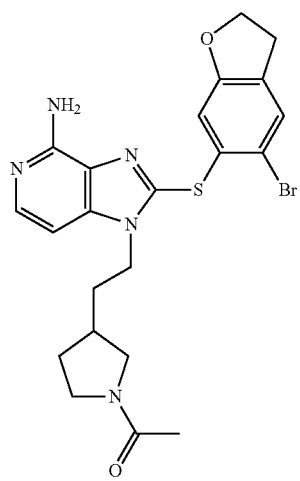
64
-continued
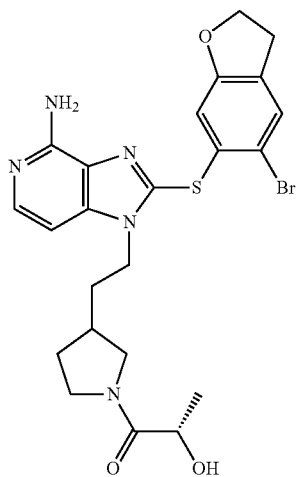
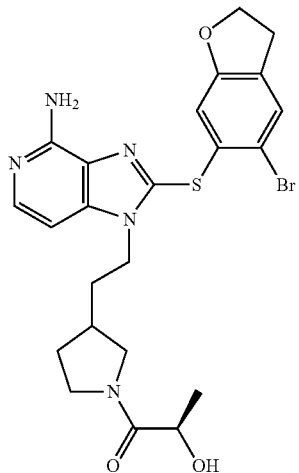
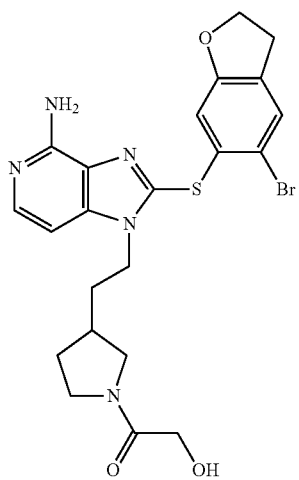

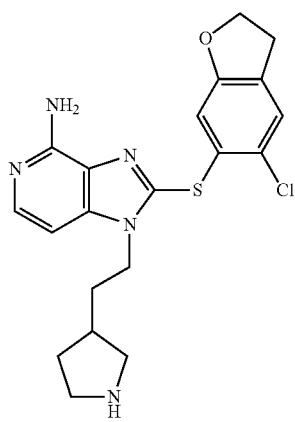
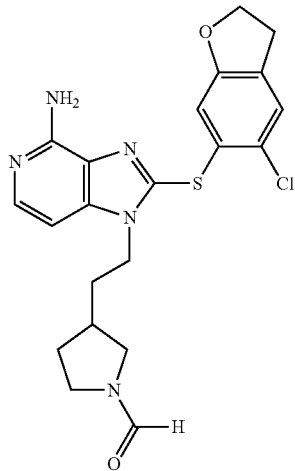
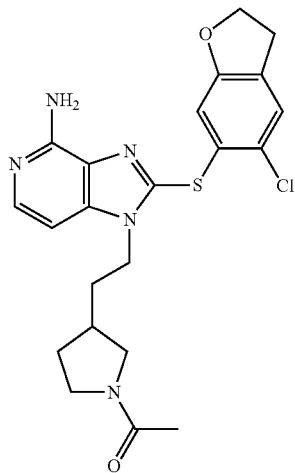
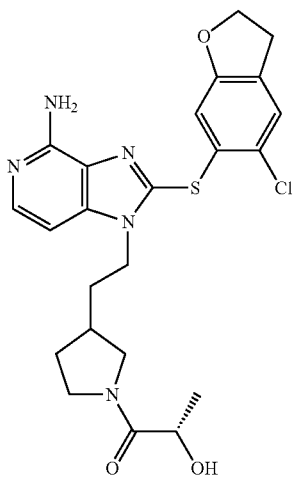
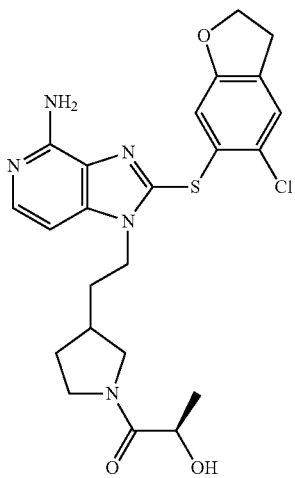
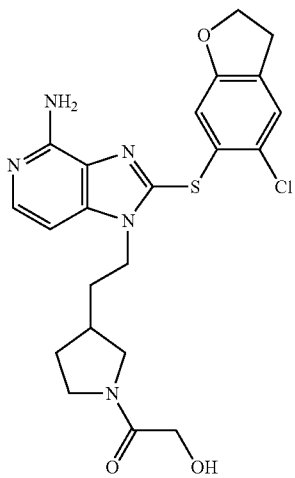

67
-continued
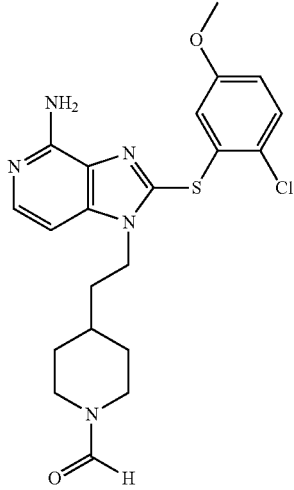
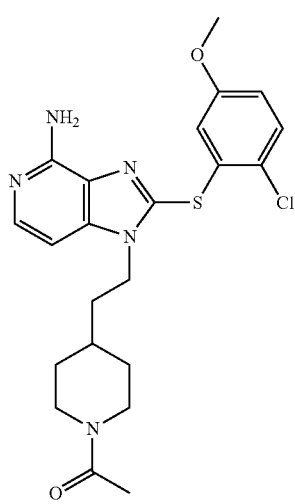
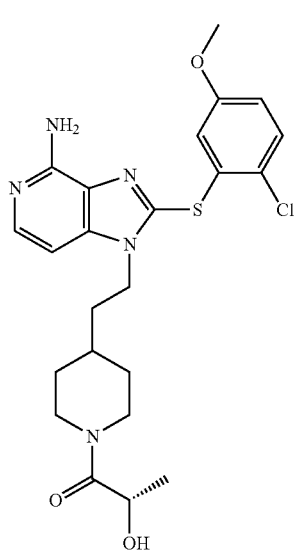
68
-continued
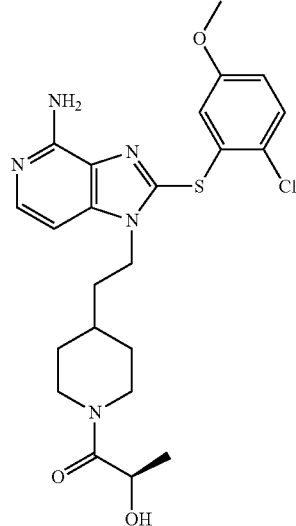
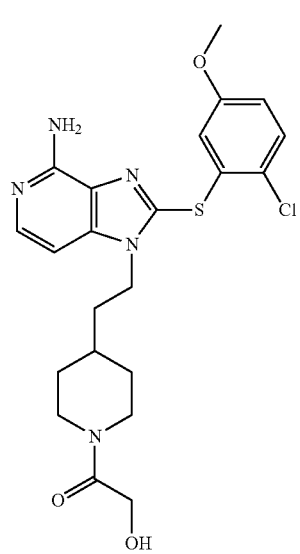
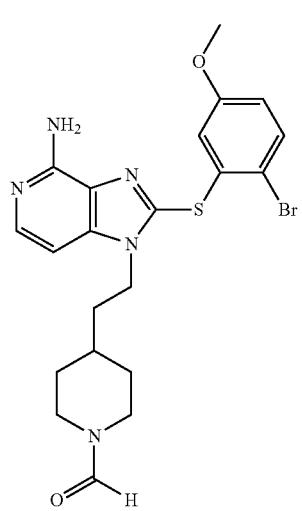

69
-continued
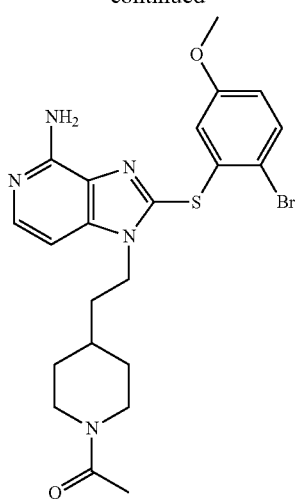
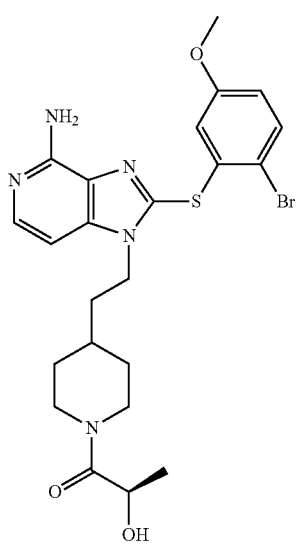
70
-continued
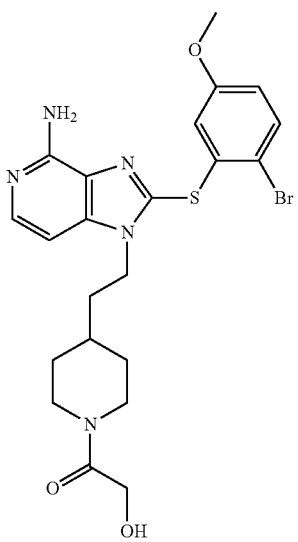
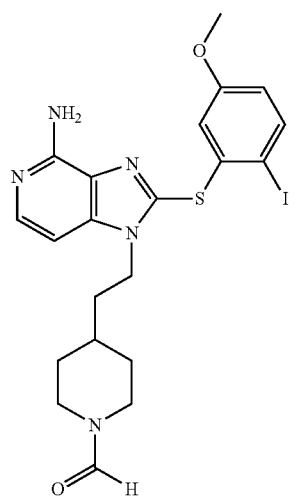

71
-continued
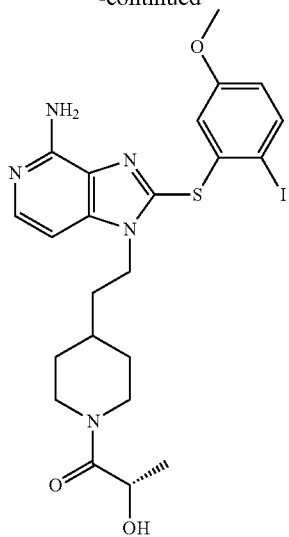
72
-continued
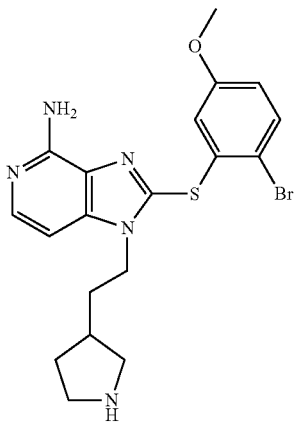
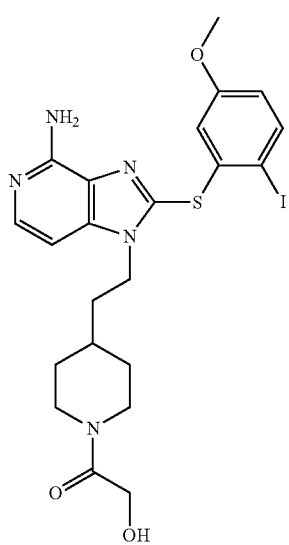
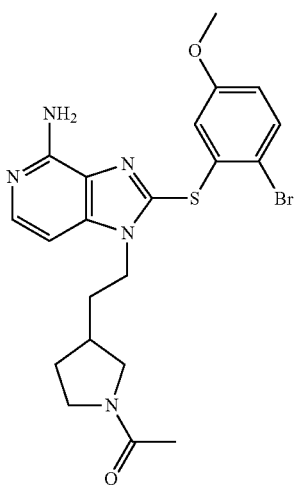

73
-continued
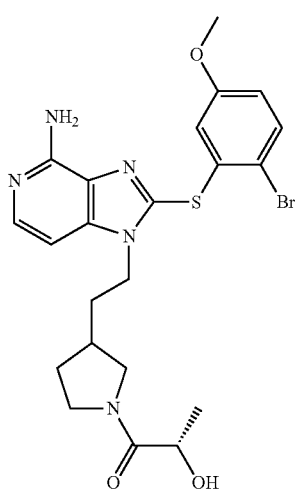
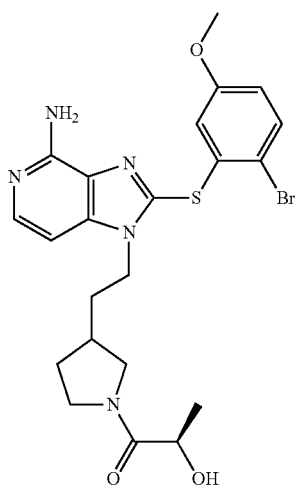
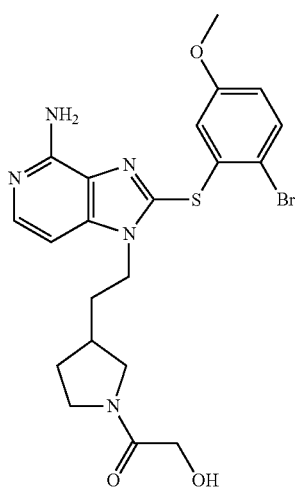
74
-continued
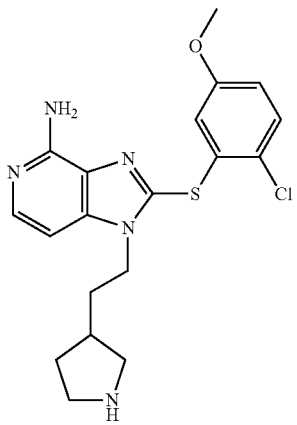
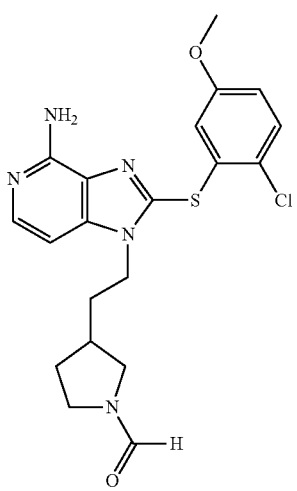
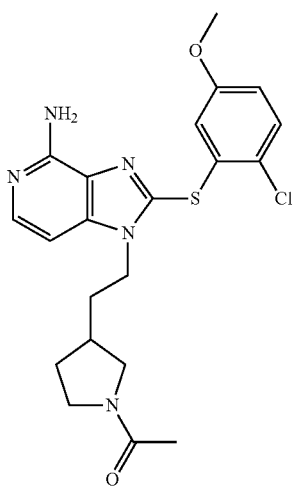

75
-continued
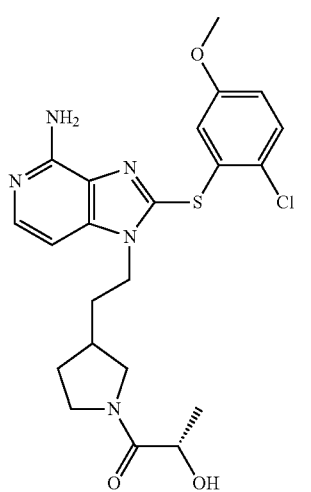
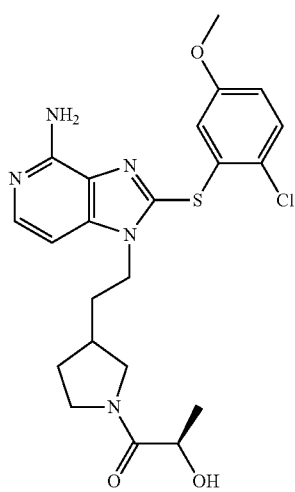
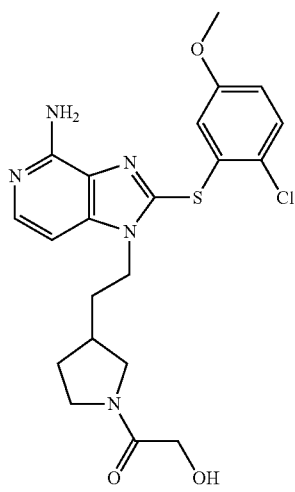
76
-continued
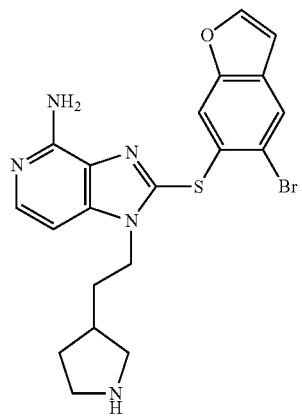
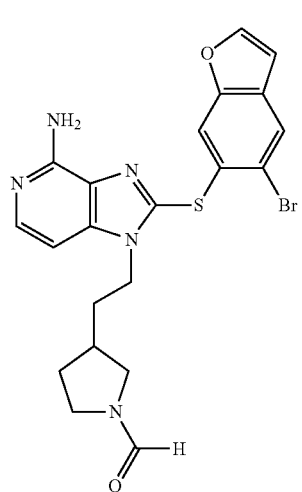
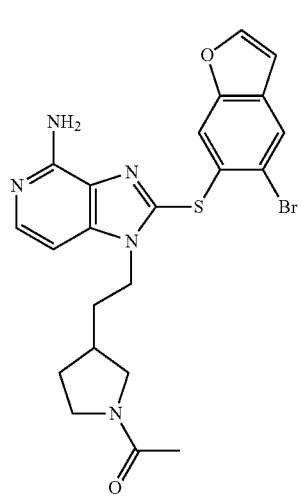

77
-continued
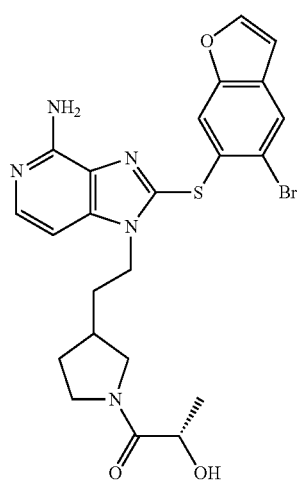
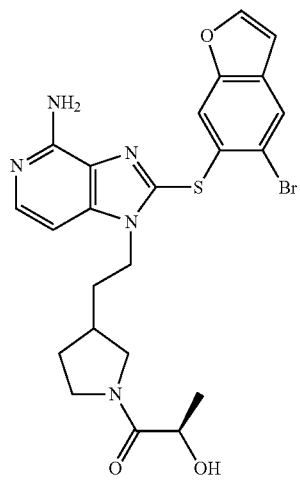
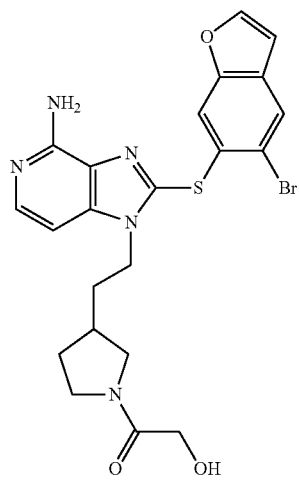
78
-continued
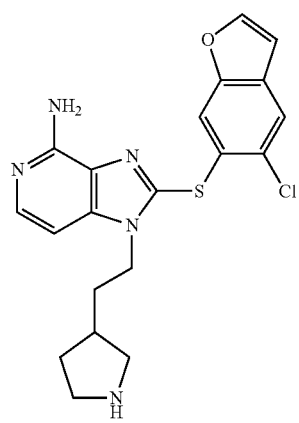
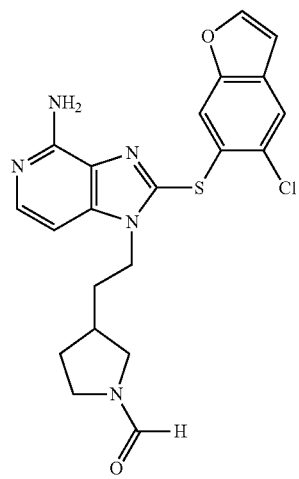
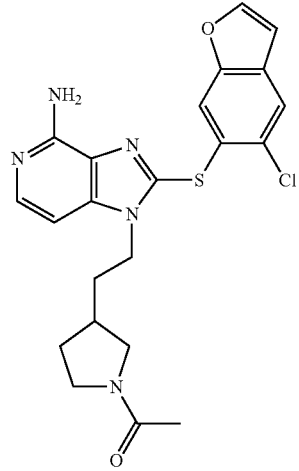

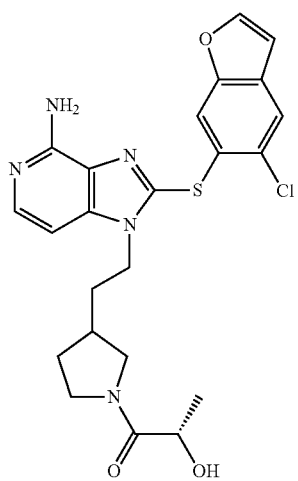
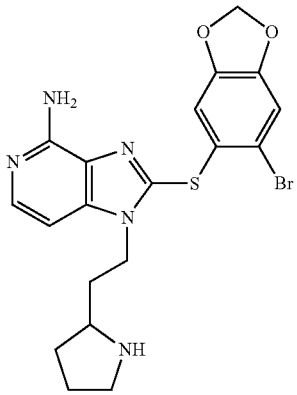
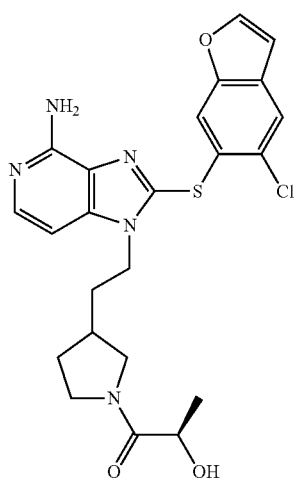
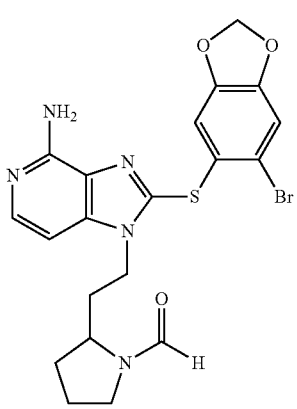
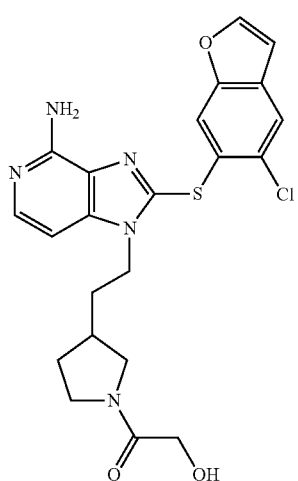
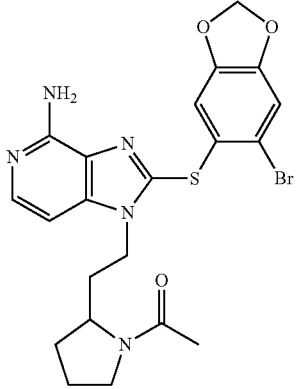
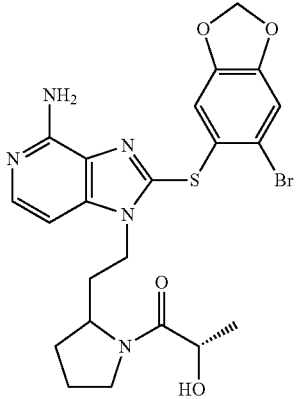

81
-continued
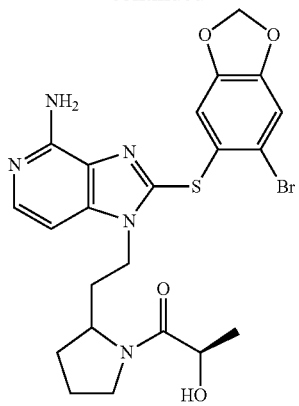
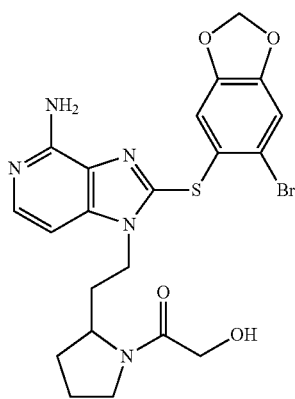
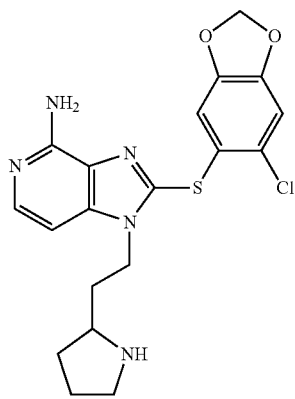
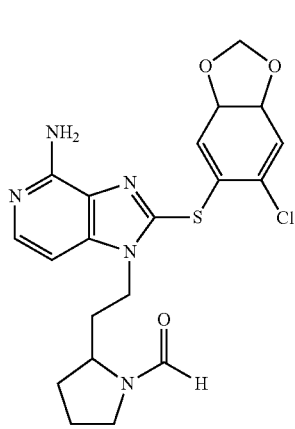
82
-continued
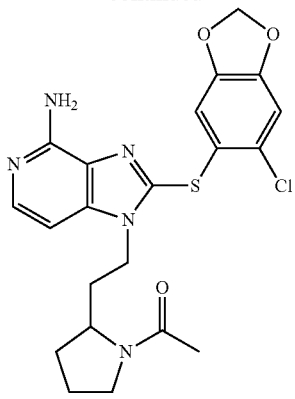
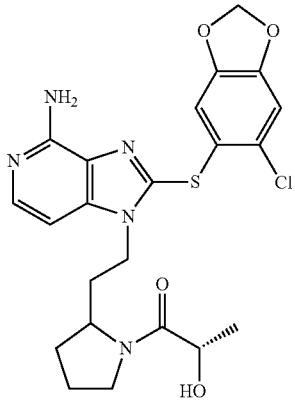
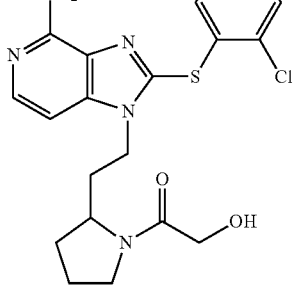

-continued

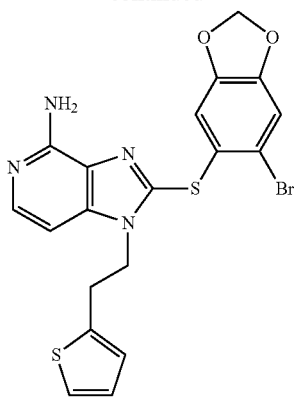

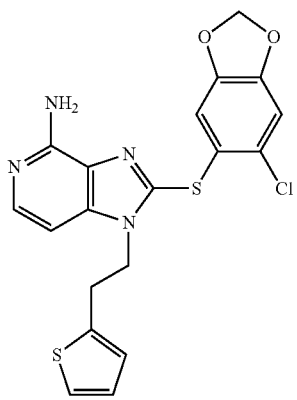

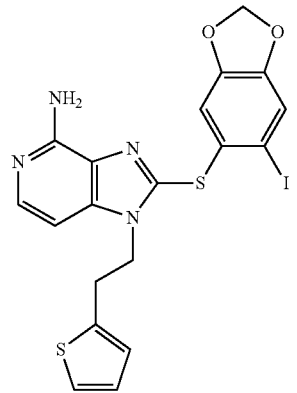

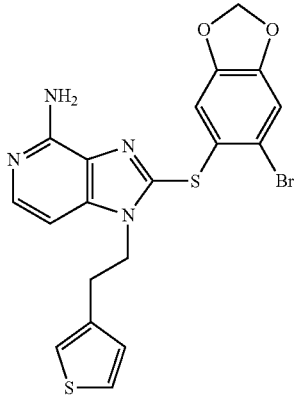

-continued

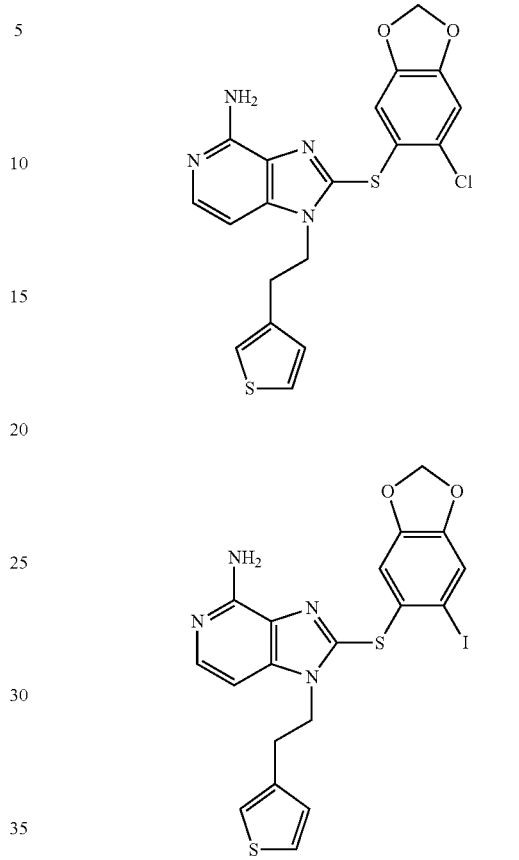

Specific synthesis examples of some of the above compounds, as well as exemplary compounds not shown above, are disclosed below.

Example 1

Step 1: 2-Chloro-N-(4-methoxybenzyl)-3-nitropyridin-4-amine

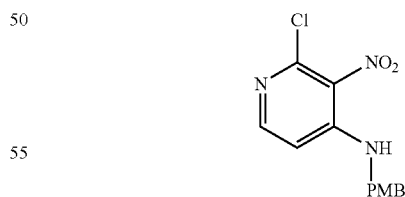

To a solution of 2,4-dichloro-3-nitropyridine (12.0 g, 62.2 mmol) in DMF (78 mL) was added NEt₃ (10.4 mL, 74.6 mmol) and p-methoxybenzylamine (8.12 ml, 62.18 mmol) at 0° C. After stirring for 10 h at rt, DMF was removed at reduced pressure. The residue was triturated with EtOAc, filtered, washed with EtOAc and hexane, and dried to afford 2-chloro-N-(4-methoxybenzyl)-3-nitropyridin-4-amine (9.29 g, 51%). Additional product (8.0 g, 44%) was obtained by column chromatography (SiO₂, eluent) from the filtrates.

Step 2: 2-Chloro-N-4-(4-methoxybenzyl)pyridine-3,4-diamine

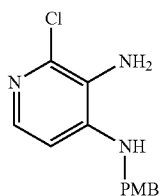

To a solution of 2-chloro-N-(4-methoxybenzyl)-3-nitropyridin-4-amine (5.0 g, 17.0 mmol) in acetic acid (85 mL) was added iron (4.76 g, 85.12 mmol). After being heated at 40° C. for 10 h, the reaction mixture was filtered, washed with CH$_2$Cl$_2$, and concentrated in vacuo. The residue was purified by column chromatography (SiO$_2$, hexane/EtOAc, 10% to 100%) to give 2-chloro-N-4-(4-methoxybenzyl)pyridine-3,4-diamine (3.2 g, 71%).

Step 3: 4-Chloro-1-(4-methoxybenzyl)-1H-imidazo[4,5-c]pyridine-2-thiol

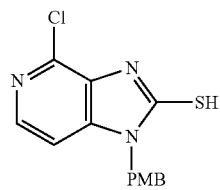

To a mixture of 2-chloro-N-4-(4-methoxybenzyl)pyridine-3,4-diamine (5.23 g, 19.83 mmol) and CS$_2$ (5.96 mL, 99.16 mmol) in EtOH (25 mL) and H$_2$O (3.8 mL), KOH (6.32 g, 99.16 mmol) was added carefully and the mixture was heated at reflux for 12 h. After cooling to rt, H$_2$O (230 mL) was added and the pH of the aqueous layer was adjusted to 7 by addition of acetic acid. The precipitated product was isolated by filtration, washed with H$_2$O, and dried to afford the title compound (5.1 g, 84%).

Step 4: 4-Amino-1-(4-methoxybenzyl)-1H-imidazo[4,5-c]pyridine-2-thiol

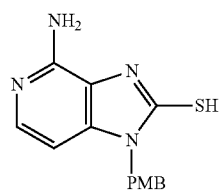

2-Chloro-N-4-(4-methoxybenzyl)pyridine-3,4-diamine (1.30 g, 5.23 mmol) and sodium amide (4900 mg, 125.5 mmol) were placed in a pressure bottle and liquid ammonia was transferred to the mixture via cannular at −78° C. The resulting mixture was slowly warmed up to rt and stirred for 15 h. After cooling to −40° C., the mixture was quenched with EtOH (8 mL) and water (400 mL) was added to the mixture. The pH of the mixture was adjusted to 7 with acetic acid. The precipitated product was filtered, washed with water, and dried to afford the title compound (1.12 g, 75%); LC-MS [M+H]$^+$ 287.0.

Step 5: 2-[(6-Bromo-1,3-benzodioxol-5-yl)sulfanyl]-1-(4-methoxybenzyl)-1H-imidazo[4,5-c]pyridin-4-amine

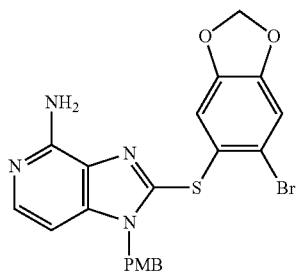

Method A:
4-Amino-1-(4-methoxybenzyl)-1H-imidazo[4,5-c]pyridine-2-thiol (1.24 g, 4.33 mmol), 5-bromo-6-iodo-1,3-benzodioxole (1.98 g, 6.06 mmol), CuI (83 mg, 0.43 mmol), neocuproine (90 mg, 0.43 mmol) and NaOtBu (624 mg, 6.50 mmol) were placed in a flask and DMF (20 mL) was added. After stirring for 10 h at 100° C., the mixture was cooled to RT, filtered, and washed with EtOAc. The combined filtrates were washed with brine, dried (Na$_2$SO$_4$), filtered, and concentrated in vacuum. The residue was triturated with CH$_2$Cl$_2$, filtered, washed with CH$_2$Cl$_2$, and air-dried to provide the title compound (1.05 g, 50%): $^1$H NMR (DMSO-d$_6$) δ 7.69 (d, J=6.0 Hz, 1H), 7.28 (s, 2H), 7.04 (d, J=8.8 Hz, 2H), 6.82 (d, J=6.0 Hz, 1H), 6.80 (d, J=8.8 Hz, 2H), 6.46 (s, 1H), 6.42 (brs, 2H), 6.03 (s, 2H), 3.68 (s, 3H); LC/MS [M+H]$^+$ 487.0.

Method B:
4-Amino-1-(4-methoxybenzyl)-1H-imidazo[4,5-c]pyridine-2-thiol (100 mg, 0.349 mmol), 5,6-dibromo-1,3-benzodioxole (196 mg, 0.698 mmol), Pd$_2$dba$_3$ (16 mg, 1.8×10$^{-2}$ mmol), Xantphos (21 mg, 3.5×10$^{-2}$ mmol), and Cs$_2$CO$_3$ (227 mg, 0.698 mmol) were placed in a vial and degassed dioxane (1.2 mL) was added to the mixture. After heating at 100° C. for 10 h, the mixture was diluted with EA, washed with brine, dried (Na$_2$SO$_4$), filtered, and concentrated in vacuum. The residue was purified by column chromatography (SiO$_2$, MeOH/CH$_2$Cl$_2$, 0 to 10%) to afford the title compound (54 mg, 31%).

Step 6: 2-[(6-Bromo-1,3-benzodioxol-5-yl)sulfanyl]-1H-imidazo[4,5-c]pyridin-4-amine

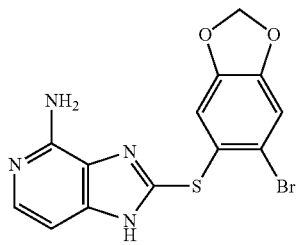

2-[(6-Bromo-1,3-benzodioxol-5-yl)sulfanyl]-1-(4-methoxybenzyl)-1H-imidazo[4,5-c]pyridin-4-amine (999 mg, 2.05 mmol) was dissolved in TFA (8 mL) and the mixture was heated at 80° C. for 7 h. Upon completion of the reaction, the mixture was concentrated in vacuum and the residual TFA was azeotropically removed with toluene. The resulting residue was diluted with water and was adjusted to pH 7 by satd. NaHCO$_3$. The product portion was extracted with EtOAc, washed with brine, dried (Na$_2$SO$_4$), filtered, and concentrated in vacuum. The residue was then triturated with EtOAc, filtered, washed with EA, and dried to afford the title compound (588 mg, 79%). Additional product (126 mg, 17%) was obtained by column (SiO$_2$, MeOH/CH$_2$Cl$_2$, 0 to 10%) purification of the combined filtrates: $^1$H NMR (DMSO-d$_6$) δ 7.53 (d, J=6.4 Hz, 1H), 7.39 (s, 1H), 7.16-7.08 (brs, 2H), 7.07 (s, 1H), 6.79 (d, J=6.4 Hz, 1H), 6.12 (s, 2H); LC-MS [M+H]$^+$ 366.97.

Step 7: 4-(2-[4-Amino-2-[(6-bromo-1,3-benzodioxol-5-yl)sulfanyl]-1H-imidazo[4,5-c]pyridin-1-yl]ethyl)piperidine-1-carbaldehyde

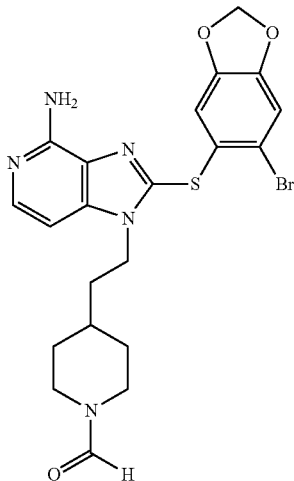

To a solution of 2-[(6-bromo-1,3-benzodioxol-5-yl)sulfanyl]-1H-imidazo[4,5-c]pyridin-4-amine (175 mg, 0.480 mmol), 2-(1-formylpiperidin-4-yl)ethyl 4-methylbenzenesulfonate (194 mg, 0.624 mmol), and Cs$_2$CO$_3$ (267 mg, 0.816 mmol) in DMF (3.0 mL) was heated at 85° C. for 10 h. After cooling to RT, the mixture was diluted with water, extracted with ethyl acetate, washed with brine, dried (Na$_2$SO$_4$), filtered, and concentrated in vacuum. The residue was triturated with EtOAc, filtered, and dried to give the title compound (102 mg, 42%): $^1$H NMR (DMSO-d$_6$) δ 7.94 (s, 1H), 7.72 (d, J=6.0 Hz, 2H), 7.39 (s, 1H), 6.79 (d, J=6.0 Hz, 2H), 6.66 (s, 1H), 6.41 (s, 2H), 6.07 (s, 2H), 4.20 (t, J=6.8 Hz, 2H), 4.10 (brd, J=13.6 Hz, 1H), 3.62 (brd, J=13.2 Hz, 1H), 2.91 (td, J=12.0, 2.4 Hz, 1H), 2.54 (m, 1H), 1.70 (t, J=6.8 Hz, 2H), 1.57-1.42 (m, 3H), 1.03 (m, 1H), 0.94 (m, 1H); LC/MS [M+H]$^+$ 504.07.

Example 2

1-[4-(2-{4-Amino-2-[(6-bromo-1,3-benzodioxol-5-yl)sulfanyl]-1H-imidazo[4,5-c]pyridin-1-yl}ethyl)piperidin-1-yl]ethanone

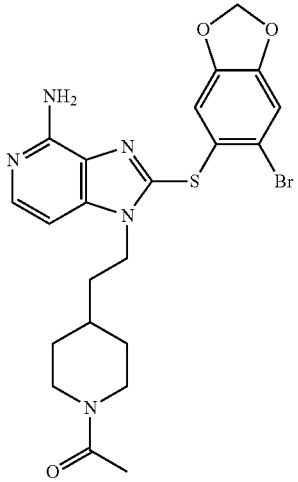

The title compound was prepared by a similar procedure described for step 7 of example 1 using 2-[(6-bromo-1,3-benzodioxol-5-yl)sulfanyl]-1H-imidazo[4,5-c]pyridin-4-amine and 2-(1-acetylpiperidin-4-yl)ethyl 4-methylbenzenesulfonate. $^1$H NMR (DMSO-d$_6$) δ; 7.70 (d, J=6.0 Hz, 1H), 7.38 (s, 1H), 6.79 (d, J=6.0 Hz, 1H), 6.66 (s, 1H), 6.42 (s, 2H), 6.07 (s, 2H), 4.30 (brd, J=13.2 Hz, 1H), 4.20 (t, J=7.2 Hz, 2H), 3.74 (brd, J=13.2 Hz, 1H), 2.89 (t, J=13.6 Hz, 1H), 2.40 (t, J=13.6 Hz, 1H), 1.96 (s, 3H), 1.66 (m, 2H), 1.56-1.51 (m, 2H), 1.43 (m, 1H), 1.08 (m, 1H), 0.94 (m, 1H); LC-MS [M+H]$^+$ 518.09.

Example 3

2-[(6-Bromo-1,3-benzodioxol-5-yl)sulfanyl]-1-[2-(2-chlorophenyl)ethyl]-1H-imidazo[4,5-c]pyridin-4-amine

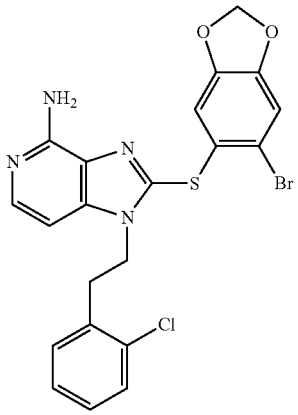

The title compound was prepared by a similar procedure described for step 7 of example 1 using 2-[(6-bromo-1,3-benzodioxol-5-yl)sulfanyl]-1H-imidazo[4,5-c]pyridin-4-amine and 1-(2-bromoethyl)-2-chloro-benzene. $^1$H NMR (DMSO-d$_6$) δ; 7.69 (d, J=6.0 Hz, 1H), 7.36 (dd, J=8.0, 1.6 Hz, 1H), 7.32 (s, 1H), 7.23 (td, J=8.0, 1.6 Hz, 1H), 7.06 (td, J=7.2, 1.6 Hz, 1H), 6.72 (d, J=6.0 Hz, 1H), 6.52 (s, 1H), 6.38 (s, 2H), 6.06 (s, 2H), 4.45 (t, J=6.8 Hz, 2H), 3.09 (t, J=6.8 Hz, 2H); LC-MS [M+H]$^+$ 502.99.

Example 4

(2S)-1-[4-(2-{4-Amino-2-[(6-bromo-1,3-benzodioxol-5-yl)sulfanyl]-1H-imidazo[4,5-c]pyridin-1-yl}ethyl)piperidin-1-yl]-1-oxopropan-2-yl acetate

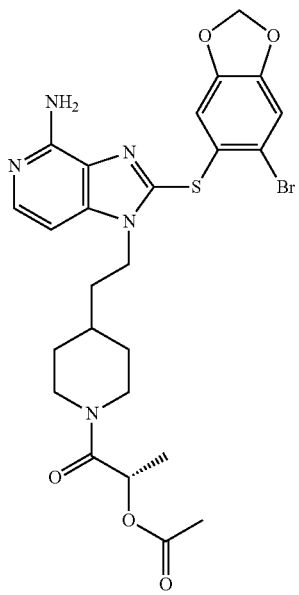

The title compound was prepared by a similar procedure described for step 7 of example 1 using 2-[(6-bromo-1,3-benzodioxol-5-yl)sulfanyl]-1H-imidazo[4,5-c]pyridin-4-amine (350 mg, 0.95 mmol) and (2S)-1-[4-(2-{[(4-methylphenyl)sulfonyl]oxy}ethyl)piperidin-1-yl]-1-oxopropan-2-yl acetate (662 mg, 1.66 mmol). LC-MS [M+H]$^+$ 590.1. This product is used for the next step without further purification.

Example 5

(2S)-1-[4-(2-{4-Amino-2-[(6-bromo-1,3-benzodioxol-5-yl)sulfanyl]-1H-imidazo[4,5-c]pyridin-1-yl}ethyl)piperidin-1-yl]-2-hydroxypropan-1-one

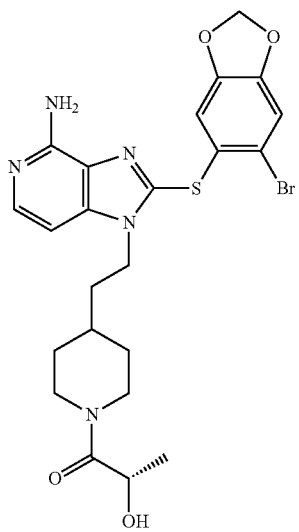

To a solution of (2S)-1-[4-(2-{4-amino-2-[(6-bromo-1,3-benzodioxol-5-yl)sulfanyl]-1H-imidazo[4,5-c]pyridin-1-yl}ethyl)piperidin-1-yl]-1-oxopropan-2-yl acetate (300 mg, 0.50 mmol) in MeOH (5 mL) was added K$_2$CO$_3$ (140 mg, 0.01 mmol) and the resulting mixture was stirred for 6 h at room temperature. After the completion of reaction, solids were collected by filtration, washed with water and dried to give the title product. $^1$H NMR (DMSO-d$_6$) δ; 7.71 (d, J=5.8 Hz, 1H), 7.37 (s, 1H), 6.79 (d, J=5.8 Hz, 1H), 6.67 (s, 1H), 6.39 (s, 2H), 6.07 (s, 2H), 5.30-5.40 (m, 1H), 4.15-4.3 (m, 3H), 3.74 (brd, J=13.2 Hz, 1H), 2.88-3.0 (m, 1H), 2.40-2.55 (m, 1H), 1.62-1.76 (m, 2H), 1.45-1.58 (m, 3H), 1.26 (t, J=8.2 Hz, 3H), 0.87-1.18 (m, 2H); TOF-MS [M+H]$^+$ 550.0915.

Example 6

2-{[6-(Dimethylamino)-1,3-benzodioxol-5-yl]sulfanyl}-1-(4-methoxybenzyl)-1H-imidazo[4,5-c]pyridin-4-amine

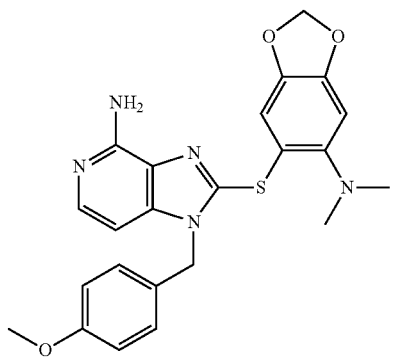

The title compound was prepared according to the experimental procedure described for step 5 of example 1. LC-MS [M+H]$^+$ 450.2.

Example 7

2-{[6-(Dimethylamino)-1,3-benzodioxol-5-yl]sulfanyl}-1H-imidazo[4,5-c]pyridin-4-amine

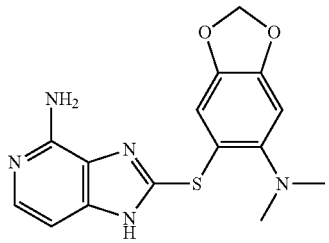

The title compound was prepared according to the experimental procedure described for step 6 of example 1. $^1$H NMR (DMSO-d$_6$) δ 12.58 (brs, 1H), 7.57 (d, J=5.6 Hz, 1H), 6.99 (s, 1H), 6.68 (d, J=5.6 Hz, 1H), 6.55 (s, 1H), 6.50-6.39 (brs, 2H), 5.98 (s, 2H), 2.61 (s, 6H); LC/MS [M+H]$^+$ 330.1.

Example 8

2-(4-Amino-2-{[6-(dimethylamino)-1,3-benzo-dioxol-5-yl]sulfanyl}-1H-imidazo[4,5-c]pyridin-1-yl)ethyl]piperidine-1-carbaldehyde

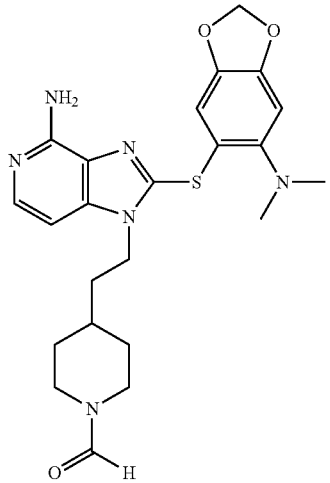

The title compound was prepared by a similar procedure described for step 7 of example 1 using 2-{[6-(dimethylamino)-1,3-benzodioxol-5-yl]sulfanyl}-1H-imidazo[4,5-c]pyridin-4-amine and 2-(1-formylpiperidin-4-yl)ethyl 4-methylbenzenesulfonate. $^1$H NMR (DMSO-$d_6$) δ 7.95 (s, 1H), 7.73 (d, J=7.6 Hz, 1H), 7.28 (d, J=7.6 Hz, 1H), 7.06 (s, 1H), 6.52 (s, 1H), 5.99 (s, 2H), 4.29 (t, J=7.6 Hz, 2H), 4.09 (brd, J=9.6 Hz, 1H), 3.61 (brd, J=8.8 Hz, 1H), 2.90 (t, J=12.4 Hz, 1H), 2.61 (s, 6H), 2.46 (m, 1H), 1.70 (t, J=12.4 Hz, 2H), 1.59 (q, J=7.6 Hz, 3H), 1.50 (m, 2H), 1.03 (m, 1H), 0.95 (m, 1H); LC/MS [M+H]$^+$ 469.20.

Example 9

(2S)-1-[4-(2-{4-Amino-2-[(6-(dimethylamino)-1,3-benzodioxol-5-yl)sulfanyl]-1H-imidazo[4,5-c]pyridin-1-yl}ethyl)piperidin-1-yl]-1-oxopropan-2-yl acetate

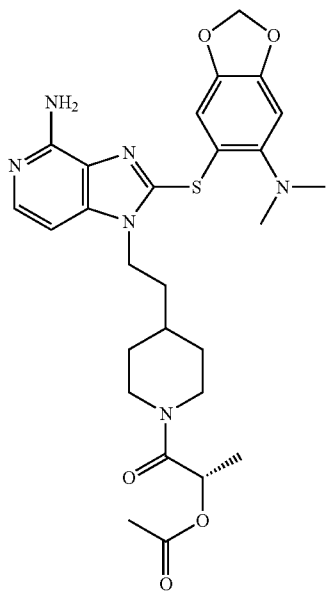

The title compound was prepared by a similar procedure described for step 7 of example 1 using 2-{[6-(dimethylamino)-1,3-benzodioxol-5-yl]sulfanyl}-1H-imidazo[4,5-c]pyridin-4-amine (150 mg, 0.45 mmol) and (2S)-1-[4-(2-{[(4-methylphenyl)sulfonyl]oxy}ethyl)piperidin-1-yl]-1-oxopropan-2-yl acetate (542 mg, 1.36 mmol). TOF LC-MS [M+H]$^+$ 555.238.

Example 10

(2S)-1-[4-(2-{4-Amino-2-[(6-(dimethylamino)-1,3-benzodioxol-5-yl)sulfanyl]-1H-imidazo[4,5-c]pyridin-1-yl}ethyl)piperidin-1-yl]-2-hydroxypropan-1-one

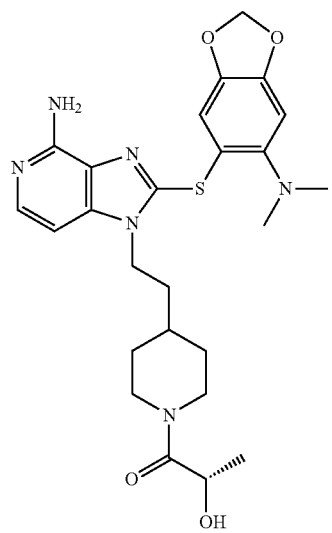

To a solution of (2S)-1-[4-(2-{4-amino-2-[(6-(dimethylamino)-1,3-benzodioxol-5-yl)sulfanyl]-1H-imidazo[4,5-c]pyridin-1-yl}ethyl)piperidin-1-yl]-1-oxopropan-2-yl acetate (171 mg, 0.32 mmol) in MeOH (3.0 mL) was added $K_2CO_3$ (89 mg, 0.64 mmol) and resulting mixture was stirred for 6 h room temperature. After completion of the reaction, the solvent was evaporated under reduced pressure and residue was purified by flash column chromatography. The product was eluted with 10% MeOH in dichloromethane. $^1$H NMR (DMSO-$d_6$) δ 7.1 (d, J=5.8 Hz, 1H), 7.0 (s, 1H), 6.78 (d, J=5.8 Hz, 1H), 6.41 (s, 2H), 6.18 (s, 1H), 5.94 (s, 2H), 7.78 (d, J=7.4 Hz, 1H), 4.37 (qin, J=5.0 Hz, 1H), 4.27 (t, J=11.3 Hz, 1H), 4.09-4.2 (m, 2H), 3.16 (d, J=5.0 Hz, 1H), 2.77-2.9 (m, 1H), 2.63 (s, 6H), 2.38-2.5 (m, 1H), 1.66 (d, J=11.7 Hz, 2H), 1.53 (q, J=6.6 Hz, 2H), 1.35-1.5 (m, 1H), 1.13 (t, J=5.0 Hz, 3H), 0.85-1.1 (m, 2H); TOF-MS [M+H]$^+$ 513.22.

Biological and Pharmacological Assays and Examples

Hsp90 Binding Assay:

The binding of exemplary compounds to purified Hsp90 can be assayed by measuring the displacement of BODIPY-labeled geldanamycin (BODIPY-GM) from purified human Hsp90, using a fluorescence polarization assay adapted from Kim et al. (*Journal of Biomolecular Screening* 2004, 9(5075-381). Compound dilutions (in 100% DMSO) are added to black-bottom 96-well plates (Greiner; 2% DMSO final), and equal volumes of BODIPY-GM (10 nM final) and purified human Hsp90 (Stressgen, SPP-770; 30 nM final) in assay buffer (20 mM HEPES-KOH pH 7.3, 50 mM KCl, 5 mM $MgCl_2$, 20 mM $Na_2MoO_4$, 0.01% NP-40, 0.1 mg/mL bovine gamma globulin [Invitrogen, P2045], 2 mM DTT) are added sequentially to yield a final volume of 50 microliters. Plates are incubated overnight at room temperature. Parallel and perpendicular fluorescence measurements are read (LJL Bio-Systems Analyst AD plate reader) at excitation/emission wavelengths of 485/530 nm. Background fluorescence (buffer only) is subtracted, and fluorescence polarization (FP) values, expressed in mP units, are calculated from parallel and perpendicular fluorescence readings as follows:

FP=(parallel−perpendicular)/(parallel+perpendicular)*1000.

Percent inhibition is calculated by normalizing the FP values to those obtained in parallel reactions containing DMSO and subtracting these normalized values from 100%. Intrinsic compound fluorescence is independently monitored, and FP data points confounded by compound fluorescence are excluded from the analysis. In some embodiments, the invention provides compounds of Formulae I through VI, wherein the compounds have an $IC_{50}$ as measured by this assay of 10 μM or less, 5 μM or less, 1 μM or less, 0.5 μM or less, 0.25 μM or less, or 0.1 μM or less.

Table 1 shows the binding of certain example compounds to purified human Hsp90 as measured by the displacement of BODIPY-labeled geldanamycin (GM) using fluorescence polarization (FP) per the procedure outlined above.

TABLE 1

| Example Compound No. | GM Displacement From Purified Hsp90 measured by FP (μM) |
|---|---|
| 1 | 5.0 |
| 2 | 5.0 |
| 3 | 2.4 |
| 5 | 1.0 |
| 8 | 0.110 |
| 9 | 0.079 |
| 10 | 0.110 |

Her2-Luciferase Assay:

HCT116 cells stably transfected with a Her2 (kinase domain)-Luciferase fusion are seeded into black 96-well plates at 10,000 cells per well in 100 microliters (DMEM supplemented with 10% serum) and incubated overnight. Compound dilutions (in 100% DMSO) are added to individual wells (0.4% DMSO final), and plates are incubated for four hours. Plates are equilibrated to room temperature (5 min), and 100 microliters Steady-Glo reagent (Promega #E2520) is added per well, and plates are incubated at room temperature for 5 minutes. Luminescence is then measured (TopCount, Perkin-Elmer).

Cytotoxicity Assay:

HCT116 cells are seeded into black 96-well plates at 5,000 cells per well in 100 microliters (DMEM supplemented with 10% serum) and are incubated overnight. Compound dilutions (in 100% DMSO) are added to individual wells (0.4% DMSO final), and plates are incubated for 72 hours. Plates are equilibrated to room temperature (5 min). Fifty microliters lysis buffer followed by 50 microliters substrate solution (ATPLite [2 step], Perkin-Elmer, #601941) is added to each well, and plates are incubated at room temperature 5 minutes. Luminescence is then measured (TopCount, Perkin-Elmer).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A compound having a structure according to Formula I or II:

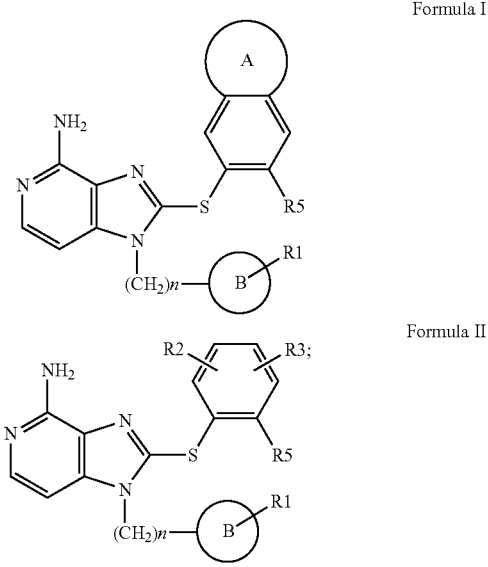

Formula I

Formula II wherein,
ring A is a saturated or partially saturated five to seven membered heterocyclic ring, or a five to seven membered heteroaryl ring, containing one or more hetero atoms independently selected from —O—, —N—, and —S—;
ring B is a saturated or partially saturated five to seven membered heterocyclic ring, or a five to seven membered heteroaryl ring, containing one or more hetero atoms independently selected from —O—, —N—, and —S—, wherein ring B is attached to the remainder of the molecule via a ring carbon;
R1 is attached to a B-ring heteroatom and is selected from H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid;
R2 and R3 are independently selected from H, halo, $C_{1-6}$ alkyl, $C_{1-6}$ alkoxy, acyl, sulfonyl, sulfamoyl, sulfonate, carboxylic acid, ester, carboxamide, and cycloalkyl;
n is 0, 1, 2, 3, 4, or 5; and
R5 is selected from F, Cl, Br, I, $CF_3$, $NO_2$, CN, $CH_2NH_2$, $CH_2NHCH_3$, $CH_2NMe_2$, —$CO_2CH_3$, $CO_2C_2H_5$, —$NHCH_3$, and —$NMe_2$;
and pharmaceutically acceptable salts thereof.

2. A compound of claim 1 having a structure according to Formula I wherein n, rings A and B, and substituents R1 and R5, are as defined in claim 1.

3. A compound of claim 1 having a structure according to Formula II wherein n, ring B, and substituents R1, R2, R3 and R5, are as defined in claim 1.

4. A pharmaceutical composition comprising a compound of claim 1 and a pharmaceutically acceptable carrier or excipient.

5. A compound of claim 1, wherein n is 1, 2, or 3 and R5 is selected from F, Cl, Br, I, $CF_3$, $NO_2$, —$NMe_2$, and CN.

6. A compound of claim 1, wherein ring B is a piperidine, pyrrolidine, homopiperidine, or thiophene ring.

7. A compound of claim 1, wherein R1 is:

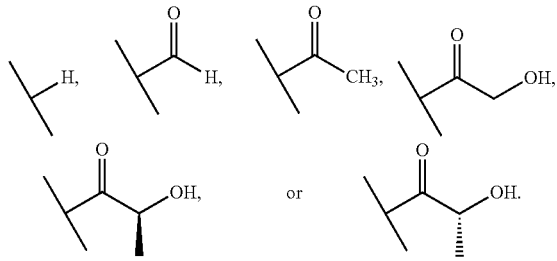

8. A compound of claim 1, having a structure according to Formula I, wherein the A ring is a fused, 5 or 6 membered ring, containing one or two oxygens.

9. A compound of claim 1, further having a structure according to Formula IV:

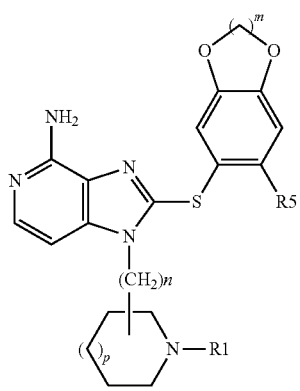

Formula IV wherein,
n is 1, 2, or 3;
m is 1 or 2;
p is 0, 1, or 2;
R1 is selected from H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid; and
R5 is selected from F, Cl, Br, I, $CF_3$, $NO_2$, —$NMe_2$, and CN.

10. A compound of claim 9, wherein R5 is selected from —$NMe_2$, F, Cl, Br, or I.

11. A compound of claim 9, wherein R1 is:

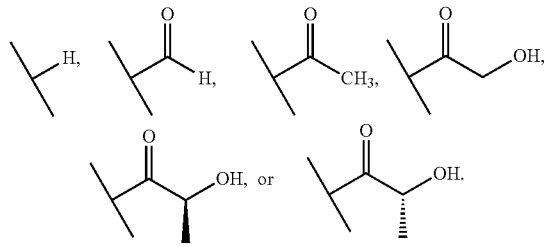

12. A compound of claim 1, further having a structure according to Formula V:

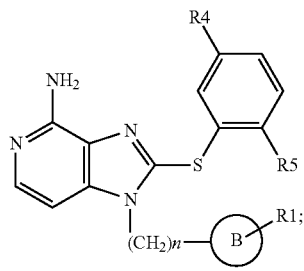

Formula V wherein,
n is 1, 2, or 3;
ring B is a saturated or partially saturated five to seven membered heterocyclic ring, or a five to seven membered heteroaryl ring, containing one or more heteroatoms independently selected from —O—, —N—, and —S—, wherein ring B is attached to the remainder of the molecule via a ring carbon;
R1 is selected from H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid; and
R4 is selected from H, halo, $C_{1-6}$ alkyl, $C_{1-6}$ alkoxy, acyl, sulfonyl, sulfamoyl, sulfonate, carboxylic acid, ester, carboxamide, and cycloalkyl; and
R5 is selected from F, Cl, Br, I, $CF_3$, $NO_2$, —$NMe_2$, and CN.

13. A compound of claim 1, further having a structure according to Formula VI:

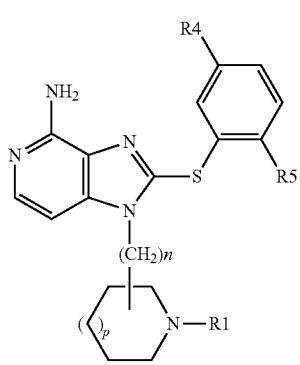

Formula VI wherein,
n is 1, 2, or 3;
p is 0, 1, or 2;
R1 is selected from H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid; and
R4 is selected from H, halo, $C_{1-6}$ alkyl, $C_{1-6}$ alkoxy, acyl, sulfonyl, sulfamoyl, sulfonate, carboxylic acid, ester, carboxamide, and cycloalkyl; and
R5 is selected from F, Cl, Br, I, $CF_3$, $NO_2$, —$NMe_2$, and CN.

14. A compound of claim 13, wherein R5 is selected from —$NMe_2$, F, Cl, Br, or I.

15. A compound of claim 13, wherein R1 is:

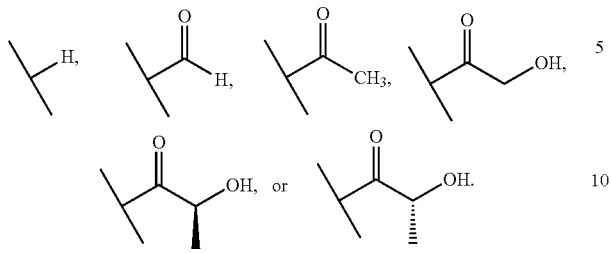

16. A compound of claim 13, wherein R4 is $C_{1-6}$ alkoxy.

17. A method of making a compound having a structure according to Formula I or II:

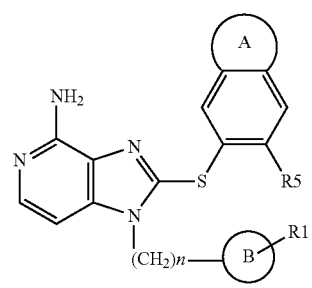

Formula I

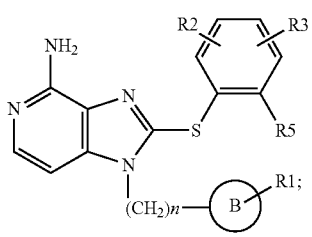

Formula II wherein,
- ring A is a saturated or partially saturated five to seven membered heterocyclic ring, or a five to seven membered heteroaryl ring, containing one or more hetero atoms independently selected from —O—, —N—, and —S—;
- ring B is a saturated or partially saturated five to seven membered heterocyclic ring, or a five to seven membered heteroaryl ring, containing one or more hetero atoms independently selected from —O—, —N—, and —S—, wherein ring B is attached to the remainder of the molecule via a ring carbon;
- R1 is attached to a B-ring heteroatom and is selected from H, $C_{1-6}$ alkyl, branched $C_{1-6}$ alkyl, formyl, acetyl, carboxylate, carboxamide, a natural or unnatural amino acid, D- or L-lactic acid, and hydroxy acetic acid;
- R2 and R3 are independently selected from H, halo, $C_{1-6}$ alkyl, $C_{1-6}$ alkoxy, acyl, sulfonyl, sulfamoyl, sulfonate, carboxylic acid, ester, carboxamide, and cycloalkyl;
- n is 0, 1, 2, 3, 4, or 5; and
- R5 is selected from F, Cl, Br, I, $CF_3$, $NO_2$, CN, $CH_2NH_2$, $CH_2NHCH_3$, $CH_2NMe_2$, —$CO_2CH_3$, $CO_2C_2H_5$, —$NHCH_3$, and —$NMe_2$;

and pharmaceutically acceptable salts thereof;

said method of making comprising:

reacting

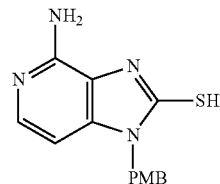

with either

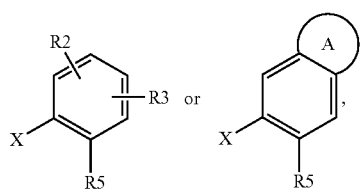

wherein X is a halogen, to form either intermediate A

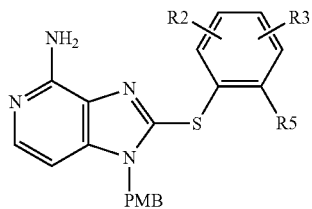

or intermediate B

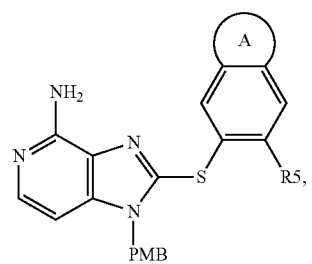

respectively;

deprotecting either intermediate A or intermediate B to form either intermediate C

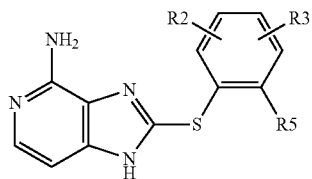

or intermediate D

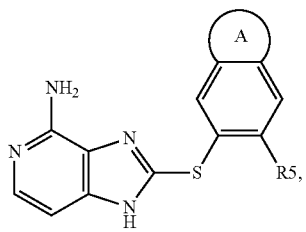

respectively;
reacting either intermediate C or intermediate D with

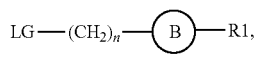

wherein LG is a leaving group, to form a compound having a structure according to Formula I or Formula II, respectively.

18. The method of claim 17, wherein said LG is selected from acetate, p-nitrobenzoate, sulfonates, methanesulfonate, p-toluenesulfonate, p-bromobenzenesulfonate, p-nitrobenzenesulfonate, fluoromethanesulfonate, difluoromethanesulfonate, trifluoromethanesulfonate, ethanesulfonate, halogens, iodine, bromine, and chlorine and reacting either intermediate C or intermediate D with

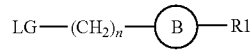

is performed under suitable conditions.

19. The method of claim 18, wherein reacting

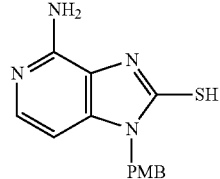

with either

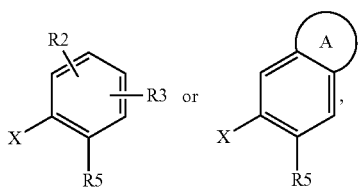

comprises utilizing a copper or palladium catalyzed coupling under suitable conditions and wherein X is iodine or bromine.

20. The method of claim 19, wherein deprotecting either intermediate A or intermediate B to form either intermediate C

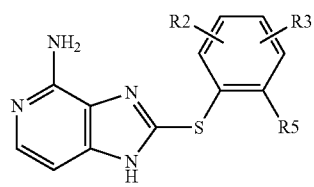

or intermediate D

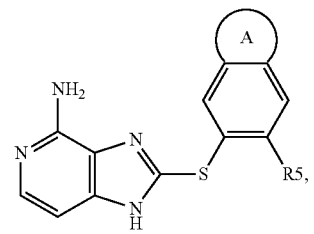

respectively, comprises dissolving either intermediate A or intermediate B is trifluoracetic acid under suitable conditions.

* * * * *